US009269343B2

(12) United States Patent

Munk et al.

(10) Patent No.: US 9,269,343 B2

(45) Date of Patent: Feb. 23, 2016

(54) METHOD OF CONTROLLING AN UPDATE ALGORITHM OF AN ADAPTIVE FEEDBACK ESTIMATION SYSTEM AND A DECORRELATION UNIT

(71) Applicant: OTICON A/S, Smørum (DK)

(72) Inventors: Steen Michael Munk, Smørum (DK); Anders Meng, Smørum (DK)

(73) Assignee: OTICON A/S, Smorum (DK)

( * ) Notice: Subject to any disclaimer, the term of this patent is extended or adjusted under 35 U.S.C. 154(b) by 245 days.

(21) Appl. No.: 14/090,847

(22) Filed: Nov. 26, 2013

(65) Prior Publication Data

US 2014/0146977 A1 May 29, 2014

Related U.S. Application Data

(60) Provisional application No. 61/730,063, filed on Nov. 27, 2012.

(30) Foreign Application Priority Data

Nov. 27, 2012 (EP) .................................... 12194329

(51) Int. Cl.

*A61F 11/06* (2006.01)
*G10K 11/16* (2006.01)
(Continued)

(52) U.S. Cl.

CPC ................ *G10K 11/175* (2013.01); *H04R 3/02* (2013.01); *H04R 25/453* (2013.01)

(58) Field of Classification Search

CPC ....... H04R 3/02; H04R 25/453; G10K 11/175
USPC ....................................................... 381/71.11
See application file for complete search history.

(56) References Cited

U.S. PATENT DOCUMENTS

| | | | |
|---|---|---|---|
| 5,748,751 | A | 5/1998 | Janse et al. |
| 7,106,871 | B1 | 9/2006 | Nielsen et al. |
| 2009/0028367 | A1 | 1/2009 | Klinkby |

FOREIGN PATENT DOCUMENTS

| | | | |
|---|---|---|---|
| EP | 1148016 | A2 | 10/2001 |
| EP | 1718110 | A1 | 11/2006 |
| EP | 2237573 | A1 | 10/2010 |
| WO | WO 95/28034 | A2 | 10/1995 |

(Continued)

OTHER PUBLICATIONS

Guilin Ma et al.: "Adaptive Feedback Cancellation With Band-Limited LPC Vocoder in Digital Hearing Aids", IEEE Transactions on Audio, Speech and Language Processing, IEEE Service Center, New York, NY, vol. 19, No. 4, May 1, 2011, pp. 677-687.*

(Continued)

*Primary Examiner* — Paul S Kim

(74) *Attorney, Agent, or Firm* — Birch, Stewart, Kolasch & Birch, LLP

(57) ABSTRACT

An audio processing device comprises a feedback estimation system for estimating feedback from an output transducer to an input transducer, the feedback estimation system comprising an adaptive filter comprising a variable filter part for filtering an input signal according to variable filter coefficients and an algorithm part comprising an adaptive algorithm for dynamically updating filter coefficients, a control unit for controlling the de-correlation unit and the adaptive algorithm, and a correlation detection unit for determining a) the auto-correlation of a signal of the forward path and providing an AC-value and/or b) the cross-correlation between two different signals of the forward path and providing an XC-value.

27 Claims, 12 Drawing Sheets

(51) Int. Cl.

| | |
|---|---|
| ***H03B 29/00*** | (2006.01) |
| ***G10K 11/175*** | (2006.01) |
| ***H04R 3/02*** | (2006.01) |
| ***H04R 25/00*** | (2006.01) |

(56) References Cited

FOREIGN PATENT DOCUMENTS

| | | | |
|---|---|---|---|
| WO | WO 2007/113282 | A1 | 10/2007 |
| WO | WO 2009/124550 | A1 | 10/2009 |

OTHER PUBLICATIONS

European Search Report Issued in EP 12194329.4, mailed on Apr. 3, 2013.

Joson et al. "Adaptive feedback cancellation with frequency compression for hearing aids," J. Acoust. Soc. Am., Dec. 1993, vol. 94, No. 6, pp. 3248-3254.

Ma et al. "Adaptive Feedback Cancellation With Band-Limited LPC Vocoder in Digital Hearing Aids," IEEE Transactions on Audio, Speech, and Laguage Processing, May 2011, vol. 19, No. 4, pp. 677-687.

* cited by examiner

METHOD OF CONTROLLING AN UPDATE ALGORITHM OF AN ADAPTIVE FEEDBACK ESTIMATION SYSTEM AND A DECORRELATION UNIT

CROSS REFERENCE TO RELATED APPLICATIONS

This nonprovisional application claims the benefit of U.S. Provisional Application No. 61/730,063 filed on Nov. 27, 2012 and to patent application Ser. No. 12/194,329.4 filed in Europe, on Nov. 27, 2013. The entire contents of all of the above applications is hereby incorporated by reference.

TECHNICAL FIELD

The present application relates to feedback estimation in audio processing devices, e.g. listening devices, such as hearing aids, in particular in acoustic situations where sound signals comprising tonal components (e.g. music) are present. The disclosure is particularly focused on minimizing audibility of artefacts.

The application furthermore relates to the use of an audio processing device, to a method of controlling an update algorithm of an adaptive feedback estimation system and to a data processing system comprising a processor and program code means for causing the processor to perform at least some of the steps of the method.

Embodiments of the disclosure may e.g. be useful in applications such as hearing aids, headsets, ear phones, active ear protection systems, handsfree telephone systems, mobile telephones, teleconferencing systems, public address systems, karaoke systems, classroom amplification systems, etc.

BACKGROUND

The following account of the prior art relates to one of the areas of application of the present application, hearing aids.

Acoustic feedback occurs because the output loudspeaker signal from an audio system providing amplification of a signal picked up by a microphone is partly returned to the microphone via an acoustic coupling through the air or other media. The part of the loudspeaker signal returned to the microphone is then re-amplified by the system before it is re-presented at the loudspeaker, and again returned to the microphone. As this cycle continues, the effect of acoustic feedback becomes audible as artefacts or even worse, howling, when the system becomes unstable. The problem appears typically when the microphone and the loudspeaker are placed closely together, as e.g. in hearing aids or other audio systems. Some other classic situations with feedback problems are telephony, public address systems, headsets, audio conference systems, car audio systems, etc. Unstable systems due to acoustic feedback tend to significantly contaminate the desired audio input signal with narrow band frequency components, which are often perceived as howl or whistle. A variety of feedback cancellation methods have been described to increase the stability of an audio processing system. The feedback path of an audio processing device, e.g. a listening device, e.g. a hearing aid, may vary over time. Adaptive feedback cancellation has the ability to track feedback path changes over time and is e.g. based on an adaptive filter comprising a linear time invariant filter (variable filter part of the adaptive filter) to estimate the feedback path, and wherein its filter weights are updated over time (e.g. calculated in an update (algorithm) part of the adaptive filter). The filter update may be calculated using stochastic gradient algorithms, including some form of the Least Mean Square (LMS) or the Normalized LMS (NLMS) algorithms. A drawback of these methods is that the estimate of the acoustic feedback path (provided by the adaptive filter) will be biased, if the input signal to the system is not white (i.e. if there is autocorrelation) because the estimate is made in a 'closed loop'. This means that the anti feedback system may introduce artefacts when there is autocorrelation (e.g. tones) in the input. 'Open loop' estimation is possible, as e.g. described in EP 2 237 573 A1.

The algorithm part of the adaptive filter comprises an adaptive algorithm for calculating updated filter coefficients for being transferred to the variable filter part of the adaptive filter. The timing of calculation and/or the transfer of updated filter coefficients from the algorithm part to the variable filter part may be controlled by an update control unit. The timing of the update (e.g. its specific point in time, and/or its update frequency) may preferably be influenced by various properties of the signal of the forward path. The control scheme may preferably be supported by various sensors of the audio processing device, e.g. a feedback detector (e.g. comprising a tone detector) for detecting whether a given frequency component is likely to be due to feedback or to be inherent in the externally originating part of the input signal (e.g. music). The timing of the adaptive algorithm for calculation and updating filter coefficients (e.g. the time interval between each calculation/update) may be defined by an adaptation rate, which again may be controlled by a step size of the adaptive algorithm.

U.S. Pat. No. 7,106,871 describes a method for canceling feedback in an acoustic system compromising a microphone, a signal path, a speaker and means for detecting presence of feedback between the speaker and the microphone, the method comprising providing a LMS algorithm for processing the signal; where the LMS algorithm operates with a predetermined adaptation speed when feedback is not present; where the LMS algorithm operates an adaptation speed faster than the predetermined adaptation speed when feedback is present, and where the means for detecting the presence of feedback is used to control the adaptation speed selection of the LMS algorithm.

WO 2007/113282 A1 describes a hearing aid comprising an adaptive feedback cancellation filter for adaptively deriving a feedback cancellation signal from a processor output signal by applying filter coefficients, and calculation means for calculating the autocorrelation of a reference signal, and an adaptation means for adjusting the filter coefficients with an adaptation rate, wherein the adaptation rate is controlled in dependency of the autocorrelation of the reference signal.

[Ma et al.; 2011] deals with feedback suppression, in particular adaptive feedback cancellation, which uses an adaptive filter to estimate the feedback path. However, a large modeling error and a cancellation of the desired signal may occur when the external input signal is correlated with the receiver input signal. It is proposed to replace the hearing-aid output with a synthesized signal, which sounds perceptually the same as or similar to the original signal but is statistically uncorrelated with the external input signal at high frequencies where feedback oscillation usually occurs.

WO 2009/124550 A1 describes an audio system comprising a signal processor for processing an audio signal, and a feedback suppressor circuit configured for modelling a feedback signal path of the audio system by provision of a feedback compensation signal based on sets of feedback model parameters for the feedback signal path that are stored in a repository for storage of the sets of feedback model parameters.

SUMMARY

An object of the present application is to provide an improved scheme for feedback estimation in an audio processing device.

Objects of the application are achieved by the invention described in the accompanying claims and as described in the following.

An Audio Processing Device:

In an aspect of the present application, an object of the application is achieved by an audio processing device comprising at least one input transducer for picking up a sound signal and converting it to at least one electric input signal and at least one output transducer for converting an electric output signal to an output sound, a forward path being defined between the at least one input transducer and the at least one output transducer, the forward path comprising a signal processing unit for processing the at least one electric input signal or a signal derived therefrom and providing a processed output signal and a de-correlation unit for de-correlating the electric output signal and the electric input signal; the audio processing device further comprising an analysis path in parallel to all or a part of the forward path, the analysis path comprising

- a feedback estimation system for estimating feedback from the at least one output transducer to the at least one input transducer and providing a corresponding feedback estimation signal, the feedback estimation system comprising an adaptive filter comprising a variable filter part for filtering an input signal according to variable filter coefficients and an algorithm part, the algorithm part comprising an adaptive algorithm for dynamically updating said filter coefficients,
- a control unit for controlling said de-correlation unit and said adaptive algorithm, and
- a correlation detection unit for determining a) the auto-correlation of a signal of the forward path and providing an AC-value and/or b) the cross-correlation between two different signals of the forward path and providing an XC-value, wherein the control unit is configured to base or influence its control of said de-correlation unit and said adaptive algorithm on said AC-value and/or said XC-value.

This has the advantage of providing an improved feedback estimate.

A signal of the forward path is a signal that originates from the at least one input transducer and is to be or has been processed by the signal processing unit and is intended to be presented to a user via the at least one output transducer.

In an embodiment, the de-correlation unit is located in the forward path between the at least one input transducer and the signal processing unit (i.e. the de-correlation unit is operationally coupled to the at least one input transducer and the signal processing unit). In an embodiment, the de-correlation unit is located in the forward path between the signal processing unit and the at least one output transducer (i.e. the de-correlation unit is operationally coupled to the signal processing unit and the at least one input transducer).

The correlation detection unit is in general adapted to provide a correlation measure indicative of the correlation between input and output signals of the forward path. Examples of such correlation measures are the auto-correlation of a signal of the forward path (value AC) and the cross-correlation between two different signals of the forward path (value XC).

In general, it is assumed that at the point in time where the new (or incremental changes to) filter coefficients are determined by the adaptive algorithm, they are also applied to the variable filter (although this needs not generally be the case). In other words, it is in the present disclosure assumed (unless otherwise explicitly indicated) that the adaptation rate of the algorithm is equal to the update rate of the variable filter. In some applications it may be advantageous to down-sample the feedback estimate, so that the update of filter coefficients is less frequent than the calculation (so that only some of the (possibly qualified) estimates are used or further processed (e.g. averaged) before being transferred as filter coefficients or update filter coefficients to the variable filter).

The application of a (small) frequency shift to a signal of the forward path provides increased de-correlation between the output and the input signal, whereby the quality of the feedback estimate provided by the adaptive algorithm is improved. However, when the level of external tones (i.e. not feedback) increases (as e.g. indicated by the correlation detector), the impact of the de-correlation (e.g. the frequency shift) becomes more and more audible. In an aspect, the present application is focused on controlling the adaptive algorithm AND the de-correlation unit in a variety of acoustic environments with a view to minimizing audibility of artefacts.

In an embodiment, the audio processing device comprises an ear piece adapted for being located in the ear canal of a user (such ear piece e.g. constituting or forming part of a hearing aid). The applied frequency shift is the more audible to the user, the more open the ear piece is (the ear piece being e.g. of the so-called receiver-in-the-ear (RITE) type). In an embodiment, the ear piece comprises a mould (e.g. adapted to the particular form of a user's ear) with a vent for minimizing occlusion. In general, the larger the vent, the larger the exchange of sound with the environment via the vent, and the more audible will the frequency shift be to the user. In an acoustic environment comprising music, the harmonic structure of the music will be disturbed by the frequency shift applied to the output signal from a speaker of the audio processing device and further disturbed by the mixture with the 'true' acoustic signal propagated through the vent.

In an embodiment, the audio processing device is configured to operate in several modes (e.g. governed by the control unit). In an embodiment, the de-correlation unit and the adaptive algorithm, respectively, may be active or inactive in various modes of operation. The 'de-correlation unit being active' is taken to mean that a de-correlation of a signal of the forward path is applied, e.g. that a frequency shift (different from zero) is applied. The 'adaptive algorithm being active' is taken to mean that an adaptation rate (and a filter coefficient update rate) is (intended to be) different from zero. 'Inactive' is taken to mean the contrary (opposite) of 'active'. In a first mode of operation, the de-correlation unit and the adaptive algorithm are both active. In a second mode of operation, the de-correlation unit is inactive (e.g. zero frequency shift), while the adaptive algorithm is active (adaptation rate larger than zero). In a third mode of operation, the de-correlation unit and the adaptive algorithm are both inactive. In a fourth mode of operation, the de-correlation unit is active, while the adaptive algorithm is inactive (adaptation rate equal to zero). In an embodiment, the audio processing device is configured to operate in several modes where in two or more separate modes the de-correlation unit and the adaptive algorithm are a) simultaneously active, b) simultaneously inactive, c) simultaneously active and inactive, respectively, or d) simultaneously inactive and active, respectively. In a preferred embodiment, the mode selection—in addition to an AC- and/or XC-value—is influenced by the status of one or more other sensors. In an embodiment, such one or more sensors comprise a feedback detector and/or a tone detector for detecting whether a signal of the forward path at a given point in time comprises frequency elements that are due to feedback from the output transducer to the input transducer and tonal frequency elements, respectively.

In an embodiment, the audio processing device comprises a memory, and is configured to store a number of previous estimates of the feedback path, in order to be able to rely on a previous estimate, if a current estimate is judged to be less optimal.

In an embodiment, the modes of operation of the audio processing device comprises a Stable mode, wherein the update rate AR of the adaptive algorithm is decreased to $AR_{min}$ and preferably stopped ($AR_{min}$=0) and a previous set of parameters is used to estimate the feedback path. In the Stable mode, de-correlation (e.g. a frequency shift FS) is preferably decreased to a minimum value ($FS_{min}$), preferably to zero ($FS_{min}$=0). In an embodiment, the Stable mode is entered, if no feedback is detected to be present (or has a high risk of emerging) in an acoustic environment comprising tonal components representing speech or music. The Stable mode is arranged to minimize the creation of audible artefacts in acoustic situations where tonal components representative of speech and/or music are prevailing (but no feedback is detected).

In a preferred embodiment, the control unit is configured to apply de-correlation and adaptation rate according to a predefined scheme including different. AC- and/or XC-values. In this embodiment, the amount of de-correlation may be different from zero or zero. Likewise, the adaptation rate of the adaptive algorithm for estimating the current feedback path may be different from zero or zero. Preferably, the control unit is configured to control the de-correlation unit and the adaptation rate of the adaptive algorithm with a view to audibility of artefacts.

In an embodiment, the audio processing device comprises a feedback cancellation system configured to subtract the feedback estimate provided by the feedback estimation system from the at least one electric input signal or a signal derived therefrom. In an embodiment, the feedback cancellation system comprises said feedback estimation system and a combination unit (e.g. a summation unit) for combining (e.g. subtracting) two input signals and providing a resulting combined output signal (termed the feedback corrected (electric) input signal or the error signal). Preferably the feedback estimate provided by the feedback estimation system is subtracted from one of the at least one electric input signals.

In an embodiment, the correlation detector is configured to estimate auto-correlation of the electric input signal. In an embodiment, the correlation detector is configured to estimate auto-correlation of the feedback corrected electric input signal. In an embodiment, the correlation detector is configured to estimate auto-correlation of the electric output signal.

In an embodiment, the correlation detector is configured to estimate cross-correlation between two signals of the forward path, a first signal tapped from the forward path before the signal processing unit (where a frequency dependent gain may be applied), and a second signal tapped from the forward path after the signal processing unit. In an embodiment, a first of the signals of the cross-correlation calculation is the electric input signal, or a feedback corrected input signal. In an embodiment, a second of the signals of the cross-correlation calculation is the processed output signal of the signal processing unit or the electric output signal (being fed to the output transducer for presentation to a user).

In an embodiment, the input side of the forward path of the audio processing device comprises an AD-conversion unit for sampling an analogue electric input signal (e.g. from the at least one input transducer) with a sampling frequency $f_s$ (e.g. 20 kHz) and providing as an output a digitized electric input signal comprising digital time samples $s_n$ of the input signal (amplitude) at consecutive points in time $t_n$=n*(1/$f_s$), n is a sample index, e.g. an integer n=1, 2, . . . indicating a sample number. The duration in time of N samples is thus given by N/$f_s$. In an embodiment, the audio processing device comprises a digital-to-analogue (DA) converter to convert a digital signal to an analogue output signal, e.g. for being presented to a user via an output transducer.

In an embodiment, the detector of auto-correlation continuously estimates the level of auto-correlation of a signal of the forward path. In an embodiment, the detector of cross-correlation continuously estimates the level of cross-correlation between two signals of the forward path. The term 'continuously' is in the present context taken to mean either (in an analogous system) constantly over time or (in a digital system) at regular points in time, said regular points in time being related to a sampling rate $f_s$ of the device (e.g. of an analogue to digital converter). In an embodiment, the detector of auto- and/or cross-correlation is/are configured to calculate new values every N·$t_s$, where N can be any integer>0 (including equal to 1), and $t_s$=1/$f_s$ is a unit (e.g. minimum) time instance of the system.

In an embodiment, the feedback estimation system is configured to provide a feedback estimate FBE at regular intervals in time (e.g. denoted n or $t_n$).

In an embodiment, the control unit is configured to decrease the adaptation rate with increasing AC-value (and/or XC-value). In an embodiment, the control unit is configured to decrease the adaptation rate with increasing AC-value (and/or XC-value), when the AC-value (and/or the XC-value) is in the range between a first value ($AC_{1\text{-}AR}$, $XC_{1\text{-}AR}$) and a second value ($AC_{2\text{-}AR}$, $XC_{2\text{-}AR}$). In an embodiment, the adaptation rate is decreased to a minimum value ($AR_{min}$) different from zero, when the AC-value (and/or the XC-value) is larger than a predefined threshold value (e.g. said second value $AC_{2\text{-}AR}$, $XC_{2\text{-}AR}$). In an embodiment, the adaptation rate is decreased to zero (adaptation is halted) when the AC-value (and/or the XC-value) is larger than a predefined threshold value (e.g. said second value $AC_{2\text{-}AR}$, $XC_{2\text{-}AR}$). This is done to avoid "damage" to the current estimate of the feedback path due to external tones. Preferably the control unit is adapted to provide that a previous ('undamaged') feedback estimate is used in the feedback cancellation instead. By the term 'external tones' is meant tones that are not due to feedback from the output transducer to an input transducer of the audio processing system. Preferably the control unit comprises a feedback detector capable of identifying whether or not a tone is an external tone (or due to feedback).

In an embodiment, the audio processing device comprises a feedback detector (e.g. comprising a tone detector) configured to indicate whether a given frequency component (e.g. a tone) of a signal of the forward path has its origin in an external signal or in feedback. Such decision (FEEDBACK or NO FEEDBACK), e.g. relating to a particular frequency component, may be embodied in a feedback control signal from the feedback detector to the control unit. In an embodiment, the control unit is configured to control the de-correlation unit and the adaptive algorithm in dependence of said feedback control signal. In an embodiment, the feedback detector is configured to provide that the feedback control signal can assume more than two values to indicate an amount of feedback (e.g. in a predefined number of steps larger than 2, or as a continuous value). In an embodiment, said scheme for controlling (e.g. decreasing) the adaptation rate with increasing AC-value is only employed when the current signal or frequency component is an external signal (e.g. based on an input from the feedback detector). In an embodiment, the control unit is configured to increase the adaptation rate and/or increase the amount of de-correlation (e.g. frequency shift) when a control signal from the feedback detector indicates that the frequency component in question is due to feedback. Such action may be advantageous, even in an acoustic environment comprising tonal elements, which in addition to feedback have their origin in an external target audio source (e.g. music), because the removal of the howl (not being part of the target (music) signal) has a top priority.

In an embodiment, the audio processing device comprises a tone detector for identifying tonal frequency components in a signal of the forward path at a given time. In an embodiment, the tone detector provides an indication (e.g. an output signal) whether or not the signal at a given time (and possibly in a given frequency band) comprises tonal components (according to a predefined definition of a tonal component). In an embodiment, the tone detector is implemented by the correlation detector, e.g. as a detector of auto-correlation or cross-correlation.

In an embodiment, the audio processing device comprises a feedback change detector configured to detect significant changes in the feedback path. Preferably, the feedback change detector provides a measure FBM of the change of the feedback path estimate from one time instance (n−1) to the next (n). In an embodiment, the measure is based on the energy content E(·) of the feedback estimate FBE, e.g. FBM(n)=E(FBE(n))−E(FBE(n−1)). In an embodiment, the measure FBM is based on the energy content (e.g. the power spectral density) of the feedback corrected input signal, e.g. the error signal e(n) (cf. FIG. 2C), e.g. FBM(n)=E(e(n))−E(e(n−1)). In an embodiment, the measure FBM is based on the energy content of the input signal before and after feedback correction input signal, e.g. FBM(n)=E(mic(n))−E(e(n)). If, e.g. the latter measure is negative, it is an indication that the feedback estimate is wrong, and this information may be used (possibly after some justification, e.g. for a number of consecutive time instances) by the control unit as an input to the control of adaptation unit and/or de-correlation unit (e.g. to decrease or stop the adaptation of the feedback estimation algorithm to not deteriorate the present estimate).

In an embodiment, the feedback estimation system is configured to provide that a previous estimate is kept, if the current estimate is concluded to be erroneous. In an embodiment, one or more previous feedback estimate(s) is/are stored in a memory, at least until a conclusion is drawn regarding the quality of the current feedback estimate. In an embodiment, the control unit is configured to base or influence its control of the de-correlation unit and/or the adaptive algorithm on an output from the feedback change detector.

The audio processing device comprises a de-correlation unit for de-correlating the electric output signal and the electric input signal. This is done to diminish the susceptibility of the feedback estimation to external tones. The de-correlation of a signal of the forward path may be introduced before or after other signal processing of the forward path. The de-correlation of a signal of the forward path may be based on different principles, e.g. the introduction of modulation of the signal, the inclusion of noise like components (e.g. the addition of a noise signal), etc. Modulation may be of any kind (e.g. frequency and/or phase and/or amplitude modulation), including the application of a systematic frequency or phase shift, e.g. a constant frequency shift or a cyclic phase shift, etc. Various de-correlation schemes are e.g. discussed in U.S. Pat. No. 5,748,751.

In an embodiment, the de-correlation unit is configured to introduce a frequency shift (e.g. a small incremental frequency shift, e.g. less than 50 Hz, such as less than 20 Hz) to a signal of the forward path, e.g. to the electric output signal. The introduction of a frequency shift, however, may in certain listening situations be audible, especially in the presence of external tones (e.g. when listening to music).

In an embodiment, the audio processing device comprises an audibility sensor/detector. The audibility sensor is preferably adapted to estimate whether or not a given artefact is audible. Preferably, the audibility sensor is adapted to identify artefacts in a signal of the forward path. In an embodiment, the audibility sensor is adapted to identify artefacts introduced by a de-correlation unit and/or from a feedback cancellation system. In an embodiment, the control unit is configured to base or influence its control of the de-correlation unit and/or the adaptive algorithm on an output from the audibility detector. In an embodiment, the audibility sensor is based on (or made dependent on) the auto-correlation and/or cross-correlation value.

To take audibility into account, it is proposed to configure the control unit to control the adaptation rate of the adaptive algorithm and the amount of de-correlation (e.g. frequency shift) applied to a signal of the forward path at a given point in time depending on current characteristics of the signal, e.g. its frequency spectrum. In an embodiment, the audio processing device comprises a frequency analyzing unit for analyzing a frequency spectrum of a signal of the forward path, e.g. the electric input signal (or a signal derived therefrom). In an embodiment, the frequency analyzing unit is configured to determine a fundamental frequency (e.g. of a voice present) in said electric input signal (or a signal derived therefrom). In an embodiment, the frequency analyzing unit is configured to determine one or more dominant frequency bands comprising a significant fraction (e.g. more than 50%, or more than 70%) of the total power of the power spectrum at a given point in time of the electric input signal (or a signal derived therefrom) (the power spectrum being e.g. represented by a power spectral density, PSD(f), the total power of the power spectrum at a given point in time being determined by a sum or integral of PSD(f) over all frequencies at the given point in time). In an embodiment, the control unit is configured to control the de-correlation unit depending on the analysis of the frequency spectrum performed by the frequency analyzing unit. In an embodiment, the (maximum) size of the frequency shift of the de-correlation unit is (e.g. dynamically) controlled depending on the analysis of the frequency spectrum, e.g. relative to a fundamental frequency or a dominant frequency band of the current frequency spectrum of a signal of the forward path. In an embodiment, the control unit is configured to provide a constant ratio of the frequency shift relative to a fundamental frequency (or to a frequency of a dominant frequency band) of a current frequency spectrum. Ideally, a larger de-correlation (e.g. frequency shift) can be applied (without audibility), the higher the fundamental frequency or dominant frequency band of the current frequency spectrum. In an embodiment, pre-determined maximum values of de-correlation (e.g. frequency shift) at different frequencies (e.g. fundamental frequencies and/or dominant frequency bands) are stored in a memory of the audio processing device, such values being related to audibility (e.g. values preserving inaudibility). Alternatively or additionally, an algorithm for determining such values may be stored in a memory. Preferably, the maximum values of de-correlation are derived to ensure that the application of de-correlation up to the maximum value (at that fundamental frequency or dominant frequency band) ensures in-audibility or minimizes audibility of the de-correlation. Maximum values of de-correlation may at certain frequencies or frequency bands be zero. For a given value of the correlation measure, the control unit is configured to use the maximum amount of de-correlation (e.g. maximum size of frequency shift) that can be applied to a signal of the forward path at a given point in time without being audible to determine the maximum adaptation rate to be applied to the adaptive algorithm for estimating feedback. At a given point in time, the amount of de-correlation (e.g. frequency shift) may be forced to be reduced (or even halted) according to the present frequency analysis scheme (e.g. if the dominant frequencies shift to lower values). Such reduction of the amount of de-correlation applied to the signal may again imply a reduced adaptation rate of the adaptive algorithm (or even a halting of adaptation altogether) depending on the current value of the correlation measure (e.g. auto-correlation of cross-correlation) of a signal or signals of the forward path.

In an embodiment, a psychoacoustic model is taken into account to determine whether or not a given artefact is audible. In an embodiment, a user's hearing threshold and/or frequency resolution is taken into account to determine whether or not a given artefact is audible.

In an embodiment, the audio processing device comprises a table (or an algorithm for) providing corresponding values of adaptation rate (AR) and amount of de-correlation (e.g. frequency shift (FS)) for corresponding values of a de-correlation measure (e.g. auto-correlation (AC) or cross-correlation (XC)) related to signals of the forward path and dominant frequencies (f) of the current frequency spectrum, as schematically indicated in the table below. In an embodiment, the subscripts 0, 1, 2, . . . , mx on AC-, XC- and f-values denote corresponding values from a relevant minimum value (or range of values) to a relevant maximum value (or range of values) for the parameter in question. For auto-correlation, e.g. $AC_0$ may correspond to a range of auto-correlation values between 0 and 0.1. The indices on the corresponding values of frequency shift (FS) and adaptation rate (AR) for a given combination of auto-correlation (or cross-correlation) and frequency only indicate the entry in question (and are not related to the actual values of FS and AR for the given table entry).

a dominant band being a frequency band comprising a significant amount, e.g. more than 50%, of the total power of the current power spectral density) of the current frequency spectrum. This may be implemented in any appropriate way, e.g. by a further detailing the above table, so that each frequency is subdivided into a number of band-widths, each having their own set of (FS, AR) values.

According to the present disclosure, the control unit is configured to control the de-correlation unit, e.g. whether or not to introduce de-correlation and/or to control the amount of de-correlation introduced. According to the present disclosure, the control unit is configured to control the de-correlation unit depending on the AC-value and/or the XC-value. In an embodiment, the control unit is configured to control the application of a frequency shift. In an embodiment, the control unit is configured to control the size of the frequency shift depending on the AC-value and/or the XC-value.

In general, (numerically) relatively low AC- or XC-values are assumed to indicate little correlation, whereas (numerically) relatively high AC- or XC-values are assumed to indicate strong correlation. If normalized, auto- or cross-correlation assume values between −1 and +1. If absolute values of normalized correlation coefficients are considered, values lie in the interval between 0 (no correlation) and 1 (perfect correlation).

In an embodiment, the control unit is configured to modify the size of the frequency shift Δf depending on the AC-value (and/or the XC-value). In an embodiment, the control unit is configured to increase the size of the frequency shift with increasing AC-value (and/or the XC-value), when the AC-value (and/or the XC-value) is in the range between a first value (e.g. $AC_{1\text{-}FS}$, $XC_{1\text{-}FS}$ in FIG. 4A) and a second (larger) value (e.g. $AC_{2\text{-}FS}$, $XC_{2\text{-}FS}$). In an embodiment, the control unit is configured to decrease the size of the frequency shift with increasing AC-value (and/or the XC-value), when the AC-value (and/or the XC-value) is in the range between a third value (e.g. $AC_{3\text{-}FS}$, $XC_{3\text{-}FS}$) and a fourth (larger) value (e.g. $AC_{4\text{-}FS}$, $XC_{4\text{-}FS}$). In an embodiment, the size of the frequency shift is zero (no frequency shift is applied) when the AC-value (and/or the XC-value) is larger than a predefined threshold value (e.g. $AC_{4\text{-}FS}$, $XC_{4\text{-}FS}$). In an embodiment, the frequency shift is kept constant (e.g. at $FS_1$ in FIG. 4A) with increasing AC-value (and/or the XC-value), when the AC-value (and/or the XC-value) is in the range between a second value (e.g. $AC_{2\text{-}FS}$, $XC_{2\text{-}FS}$) and a third value (e.g. $AC_{3\text{-}FS}$, $XC_{3\text{-}FS}$).

| | f | | | | |
|---|---|---|---|---|---|
| AC/XC | $f_0$ | $f_1$ | $f_2$ | . . . | $f_{mx}$ |
| $AC/XC_0$ | $(FS,AR)_{00}$ | $(FS,AR)_{01}$ | $(FS,AR)_{02}$ | $(FS,AR)_{0..}$ | $(FS,AR)_{0mx}$ |
| $AC/XC_1$ | $(FS,AR)_{10}$ | $(FS,AR)_{11}$ | $(FS,AR)_{12}$ | $(FS,AR)_{1..}$ | $(FS,AR)_{1mx}$ |
| $AC/XC_2$ | $(FS,AR)_{20}$ | $(FS,AR)_{21}$ | $(FS,AR)_{22}$ | $(FS,AR)_{2..}$ | $(FS,AR)_{2mx}$ |
| . . . | $(FS,AR)_{..0}$ | $(FS,AR)_{..1}$ | $(FS,AR)_{..2}$ | $(FS,AR)_{....}$ | $(FS,AR)_{..mx}$ |
| $AC/XC_{mx}$ | $(FS,AR)_{mx0}$ | $(FS,AR)_{mx1}$ | $(FS,AR)_{mx2}$ | $(FS,AR)_{mx..}$ | $(FS,AR)_{mxmx}$ |

In at least one of the table entries of the above table, a value of the frequency shift may be equal to zero (no frequency shift applied). In at least one of the table entries, a value of the adaptation rate may be equal to zero (no calculation of new filter coefficients/no update of the feedback estimate). In at least one of the table entries, a value of the frequency shift as well as a value of the adaptation rate may be equal to zero. In an alternative embodiment, none of the table entries of the above table represent situations where the frequency shift as well as the adaptation rate is zero.

In an embodiment, the control unit is configured to control the de-correlation unit and/or the adaptive algorithm depending on a bandwidth of a dominant frequency (e.g. a fundamental frequency or the width of a dominant frequency band, For configurations (e.g. modes of operation) without application of specific de-correlation actions (e.g. frequency shift), a preferred embodiment is configured to allow normal adaptation, if the AC-value (and/or the XC-value) is below a certain threshold value (e.g. $AC_{2\text{-}AR}$, $XC_{2\text{-}AR}$ in FIG. 3B). Above this threshold value, adaptation is preferably halted (no update of filter coefficients is performed, to avoid that the current feedback path estimate degrades).

For configurations (e.g. modes of operation) implementing specific de-correlation actions (e.g. frequency shift), adaptation of the feedback estimate (update of filter coefficients), even at relatively high levels of external tones, (=>relatively high auto-correlation and/or cross-correlation values) is possible without severe effects to the feedback path estimate. However, as the level of external tones increases further, the impact of the de-correlation (e.g. frequency shift) becomes more and more audible. In a preferred embodiment, application of de-correlation, e.g. frequency shift, is stopped, when the AC-value (and/or the XC-value) is larger than a predefined threshold value (e.g. $AC_{4\text{-}FS}$, $XC_{4\text{-}FS}$ in FIG. 4). Preferably, the adaptation of the feedback estimate is also halted (the adaptation rate of the adaptive algorithm is set equal to zero). Preferably, the application or not (activation or deactivation) of de-correlation measures (e.g. frequency shift) is influenced by a feedback detector indicating whether or not feedback is present at a given point in time (and frequency). In a preferred mode of operation, de-correlation is activated, if feedback is detected.

The AC-values (and/or the XC-values) at which the adaptation rate is decreased or set equal to zero (cf. FIG. 3) may be equal to or different from the AC-values (and/or XC-values) at which the frequency shift is decreased or set equal to zero (cf. FIG. 4).

In an embodiment, the control unit is configured to provide that the de-correlation unit is inactive (e.g. providing that no frequency shift is applied to a signal of the forward path, FS=0) AND to allow the adaptive algorithm to adapt the feedback estimate according to a normal scheme, e.g. at a normal rate (e.g. a predefined fixed rate, e.g. $AR=AR_{max}$ in FIG. 5B), when the AC-values (and/or the XC-values) are below a predefined first threshold value ($AC_{th1}$, $XC_{th1}$ in FIG. 5B).

In an embodiment, the control unit is configured to provide that the de-correlation unit is active (e.g. providing that a predefined frequency shift (e.g. $FS=FS_{max}$ in FIG. 5B) is applied to a signal of the forward path) AND to allow the adaptive algorithm to adapt the feedback estimate according to a normal scheme, e.g. at a normal rate (e.g. a predefined fixed rate, e.g. $AR=AR_{max}$ in FIG. 5B), when the AC-values (and/or the XC-values) are in a range above a predefined first threshold value ($AC_{th1}$, $XC_{th1}$) and below a second predefined threshold value ($AC_{th2}$, $XC_{th2}$).

In an embodiment, the control unit is configured to provide that the de-correlation unit is inactive (e.g. FS=0 in FIG. 5B) AND the adaptive algorithm is inactive (halted, adaptation rate set equal to zero, AR=0 in FIG. 5B) when the AC-values (and/or the XC-values) are larger than a predefined threshold value (e.g. the second predefined threshold value $AC_{th2}$, $XC_{th2}$).

In an embodiment, the audio processing device is adapted to provide a frequency dependent gain to compensate for a hearing loss of a user. In an embodiment, the signal processing unit is adapted to enhance the input signal(s), e.g. to compensate for a hearing loss of a particular user.

In an embodiment, the audio processing device comprises at least two input transducers. In an embodiment, the at least one input transducer comprise(s) a microphone. In an embodiment, the at least two input transducers comprise a directional microphone system adapted to enhance a target acoustic source among a multitude of acoustic sources in the local environment of the user wearing the audio processing device. In an embodiment, the directional system is adapted to detect (such as adaptively detect) from which direction a particular part of the microphone signal originates.

In an embodiment, the audio processing device comprises a separate feedback estimation system for each input transducer. In an embodiment, the audio processing device comprises a separate feedback cancellation system for each input transducer.

In an embodiment, the output transducer comprises a vibrator of a bone conducting hearing device. In an embodiment, the output transducer comprises a receiver (speaker) for converting the electric output signal to an acoustic signal for presentation to a user of the audio processing device. In an embodiment, the audio processing device comprises at least two output transducers.

In an embodiment, the audio processing device is portable device, e.g. a device comprising a local energy source, e.g. a battery, e.g. a rechargeable battery.

In an embodiment, the analysis path—in addition to providing an acoustic feedback estimate—comprises functional components for analyzing the input signal (e.g. determining a level, a modulation, a type of signal, etc.). In an embodiment, some or all signal processing of the analysis path and/or the forward path is conducted in the frequency domain. In an embodiment, some or all signal processing of the analysis path and/or the forward path is conducted in the time domain. In an embodiment, some or all signal processing of the forward path is conducted in the time domain, whereas some or all signal processing of the analysis path in the frequency domain.

In an embodiment, the signal processing in the analysis path (feedback estimation, etc.) is performed fully or partially in the frequency domain, cf. FIG. 2F. In an embodiment, the determination of filter coefficients (or update filter coefficients) by the algorithm part of the adaptive filter of the feedback estimation system is performed in the frequency domain (sub-bands). In an embodiment, the filter coefficients (or update filter coefficients) provided by the algorithm part are converted to the time domain and applied to a filter for filtering a signal of the forward path in the time domain. Alternatively, the feedback path estimation and processing in the forward path may be performed fully in the frequency domain (or fully in the time domain).

In an embodiment, the audio processing device, e.g. the microphone unit, and or the transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the audio processing device from a minimum frequency $f_{min}$ to a maximum frequency $f_{max}$ comprises a part of the typical human audible frequency range from 20 Hz to 20 kHz, e.g. a part of the range from 20 Hz to 12 kHz. In an embodiment, a signal of the forward and/or analysis path of the audio processing device is split into a number NI of frequency bands, where NI is e.g. larger than 5, such as larger than 10, such as larger than 50, such as larger than 100, such as larger than 500, at least some of which are processed individually. In an embodiment, the audio processing device is/are adapted to process a signal of the forward and/or analysis path in a number NP of different frequency channels ($NP \leq NI$). The frequency channels may be uniform or non-uniform in width (e.g. increasing in width with frequency), overlapping or non-overlapping.

In an embodiment, the audio processing device comprises a level detector (LD) for providing an output indicative of the level of an input signal (e.g. on a band level and/or of the full (wide band) signal). The current level of the electric input signal picked up from the user's acoustic environment is e.g. a classifier of the current acoustic environment. In an embodiment, the control unit is configured to base or influence its control of the adaptation rate and/or its control of the de-correlation unit on the output from the level detector.

In a particular embodiment, the audio processing device comprises a voice detector (VD) for providing an output indicative of whether or not an input signal comprises a voice (e.g. speech) signal (at a given point in time). A voice signal is in the present context taken to include a speech signal from a human being. It may also include other forms of utterances generated by the human speech system (e.g. singing). In an embodiment, the voice detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only comprising other sound sources (e.g. artificially generated sounds, e.g. noise). In an embodiment, the control unit is configured to base or influence its control of the adaptation rate and/or its control of the de-correlation unit on the output from the voice detector.

In an embodiment, the audio processing device comprises an own voice detector (OD) for providing an output indicative of whether a given input sound (e.g. a voice) originates from the voice of the user of the device. In an embodiment, the audio processing device is adapted to be able to differentiate between a user's own voice and another person's voice and possibly from NON-voice sounds. In an embodiment, the control unit is configured to base or influence its control of the adaptation rate and/or its control of the de-correlation unit on the output from the own voice detector.

In an embodiment, the audio processing device comprises a listening device, e.g. a hearing aid, e.g. a hearing instrument (e.g. a hearing instrument adapted for being located at the ear or fully or partially in the ear canal of a user), e.g. a headset, an earphone, an ear protection device or a combination thereof.

Use:

In an aspect, use of an audio processing device as described above, in the 'detailed description of embodiments' and in the claims, is moreover provided. In an embodiment, use is provided in a system comprising audio distribution, e.g. a system comprising a microphone and a loudspeaker in sufficiently close proximity of each other to cause feedback from the loudspeaker to the microphone during operation by a user. In an embodiment, use is provided in a system comprising one or more hearing instruments, headsets, ear phones, active ear protection systems, etc., e.g. in handsfree telephone systems, teleconferencing systems, public address systems, karaoke systems, assistive listening systems, classroom amplification systems, etc.

A Method:

In an aspect, a method of controlling an update algorithm of an adaptive feedback estimation system in an audio processing device, the audio processing device comprising at least one input transducer for picking up a sound signal and converting it to at least one electric input signal and at least one output transducer for converting an electric output signal to an output sound, a forward path being defined between the at least one input transducer and the at least one output transducer, the forward path comprising a signal processing unit for processing the at least one electric input signal or a signal derived therefrom and providing a processed output signal and a de-correlation unit for de-correlating the electric output signal and the electric input signal is furthermore provided by the present application. The method comprises

- providing an estimate of the feedback from the at least one output transducer to the at least one input transducer by providing an adaptive algorithm for dynamically updating filter coefficients of a variable filter with a controllable adaption rate;
- determining a) the auto-correlation of a signal of the forward path and providing an AC-value and/or b) the cross-correlation between two different signals of the forward path and providing an XC-value;
- controlling said de-correlation unit and said adaptive algorithm dependent on said AC-value and/or said XC-value.

It is intended that some or all of the structural features of the device described above, in the 'detailed description of embodiments' or in the claims can be combined with embodiments of the method, when appropriately substituted by a corresponding process and vice versa. Embodiments of the method have the same advantages as the corresponding devices.

A Computer Readable Medium:

In an aspect, a tangible computer-readable medium storing a computer program comprising program code means for causing a data processing system to perform at least some (such as a majority or all) of the steps of the method described above, in the 'detailed description of embodiments' and in the claims, when said computer program is executed on the data processing system is furthermore provided by the present application. In addition to being stored on a tangible medium such as diskettes, CD-ROM-, DVD-, or hard disk media, or any other machine readable medium, and used when read directly from such tangible media, the computer program can also be transmitted via a transmission medium such as a wired or wireless link or a network, e.g. the Internet, and loaded into a data processing system for being executed at a location different from that of the tangible medium.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which.

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

Figure 1A:
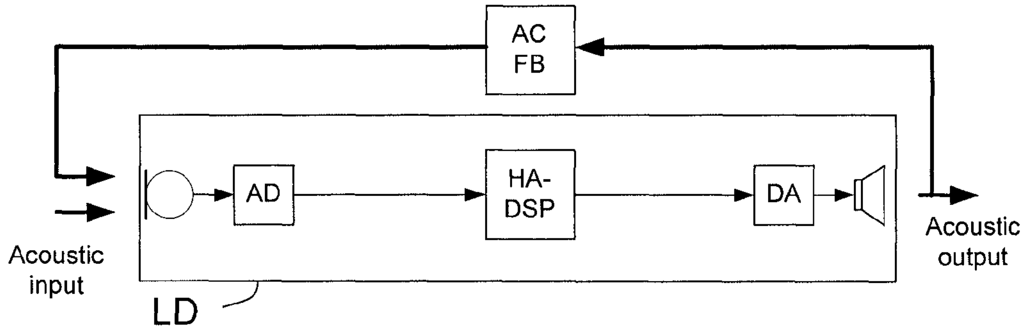
FIGS. 1A-1D show four embodiments of a prior art listening device audio processing device, e.g. a listening device.
Figure 1B:
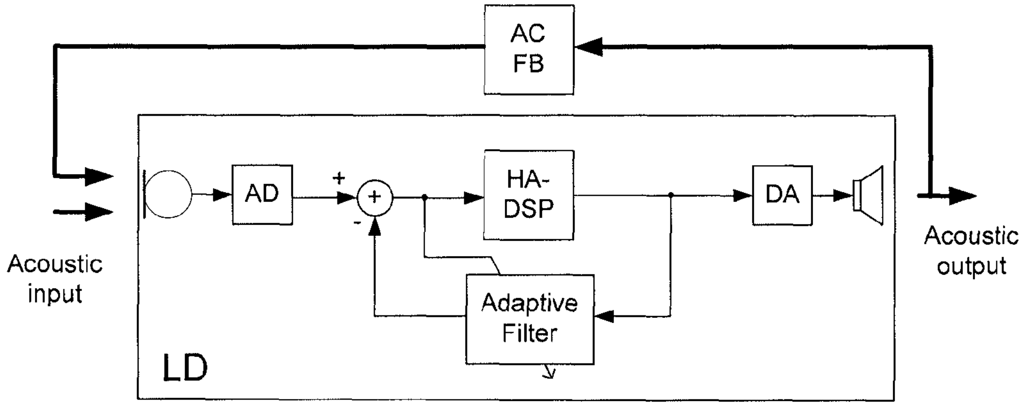
Figure 1C:
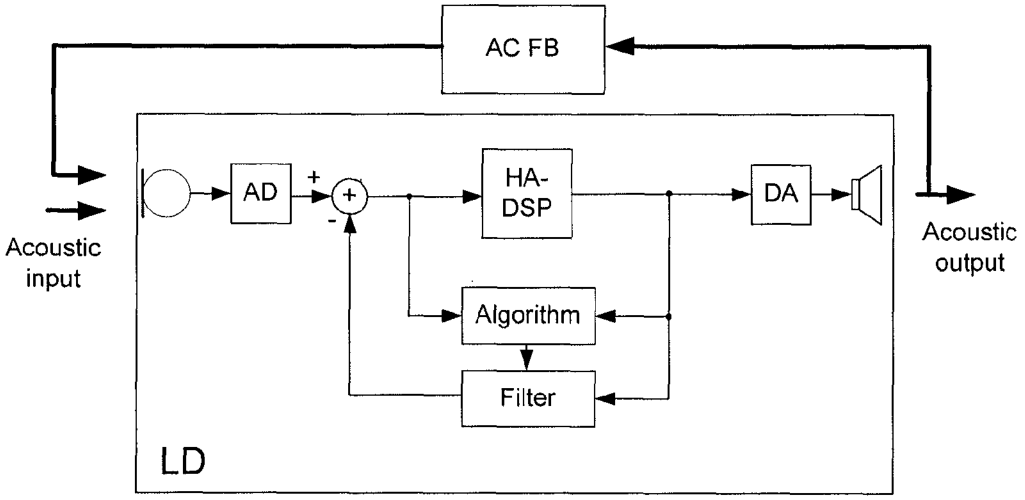
Figure 1D:
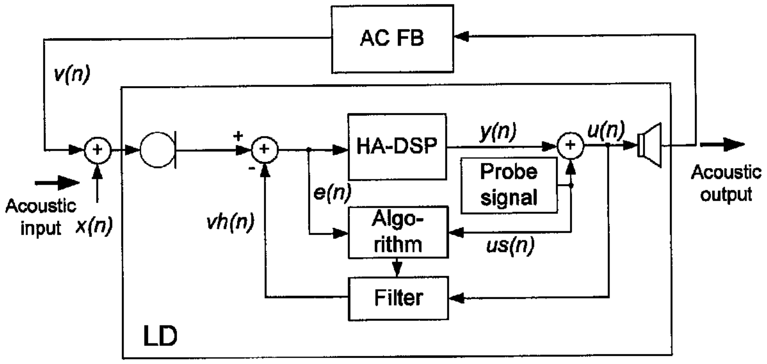

FIGS. 1A-1D show four embodiments of a prior art listening device audio processing device, e.g. a listening device. In the following the audio processing device is exemplified as a hearing aid, but the description might as well relate to other audio processing devices prone to acoustic feedback. FIG. 1A shows a simple hearing aid comprising a forward or signal path from an input transducer to an output transducer, a forward path being defined there between and comprising a processing unit HA-DSP for applying a frequency dependent gain to the signal picked up by the microphone and providing an enhanced signal to the output transducer. Additionally, the forward path comprises analogue-to-digital (AD) and digital-to-analogue (DA) converters to enable digital processing. Appropriate time-to-frequency and frequency-to-time transformation units may be included to allow processing in the forward path (or elsewhere, e.g. in an analysis path) in the frequency domain. Hearing aid feedback cancellation systems (for reducing or cancelling acoustic feedback from an ‘external’ feedback path (AC FB) from output to input transducer of the hearing aid) may comprise an adaptive filter (‘Adaptive filter’ in FIG. 1B), which is controlled by a prediction error algorithm, e.g. an LMS (Least Means Squared) algorithm, in order to predict and (ideally) cancel the part of the microphone signal that is caused by feedback (from the receiver of the hearing aid to the microphone(s)). FIGS. 1B and 1C illustrate examples of this. The adaptive filter (in FIG. 1C comprising a variable ‘Filter’ part end a prediction error or update or ‘Algorithm’ part) is (here) aimed at providing a good estimate of the ‘external’ feedback path from the (input to the) digital-to-analogue (DA) converter to the (output from the) analogue-to-digital (AD) converter. The prediction error algorithm uses a reference signal (e.g. the output signal (=input signal to the DA converter in FIG. 1B, 1C)) together with a signal originating from the microphone signal to find the setting of the adaptive filter that minimizes the prediction error, when the reference signal is applied to the adaptive filter. The forward path of the hearing aid comprises signal processing (HA-DSP in FIG. 1) e.g. adapted to adjust the input signal to the impaired hearing of a user. The estimate of the feedback path provided by the adaptive filter is (cf. FIG. 1B, 1C, 1D) subtracted from the microphone signal in sum unit ‘+’, providing a so-called ‘error signal’ (or feedback-corrected signal), which is fed to the processing unit HA-DSP and to the algorithm part of the adaptive filter (FIG. 1C, 1D). To provide an improved de-correlation between the output and input signal, it may be desirable to add a probe signal us(n) to the output signal, n being a time instance parameter. The probe signal us(n) can be used as the reference signal to the algorithm part of the adaptive filter, as shown in FIG. 1D (output of ‘Probe signal’ generator in FIG. 1D), and/or it may be mixed with the ordinary output of the hearing aid to form the reference signal. In FIG. 1D the probe signal us(n) is mixed with the output signal y(n) of the signal processing unit HA-DSP in sum unit ‘+’ resulting in output signal u(n) fed to the output transducer (speaker unit) and to the variable filter part of the adaptive filter. On the input side, the target signal is termed x(n) and the feedback signal v(n). The estimated feedback signal vh(n) from the adaptive filter is subtracted from the microphone signal in sum unit ‘+’ whose resulting output (error signal) e(n) is fed to the signal processing unit HA-DSP as well as to the algorithm part of the adaptive filter. In general, the probe signal may be generated in any appropriate way, e.g. fulfilling the requirements of non-correlation of (or decreased correlation between) input and output signal.

Figure 2A:
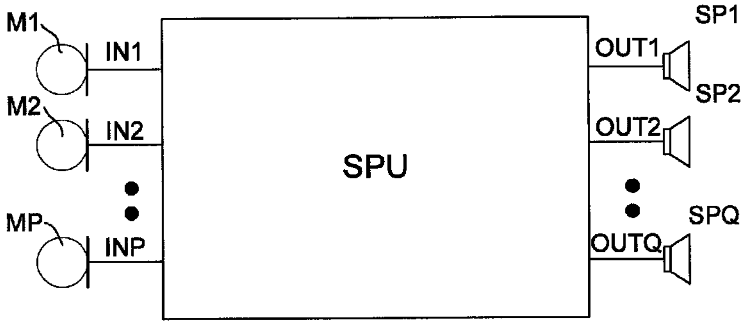
FIGS. 2A-2F show six embodiments of an audio processing device according to the present disclosure.
Figure 2B:
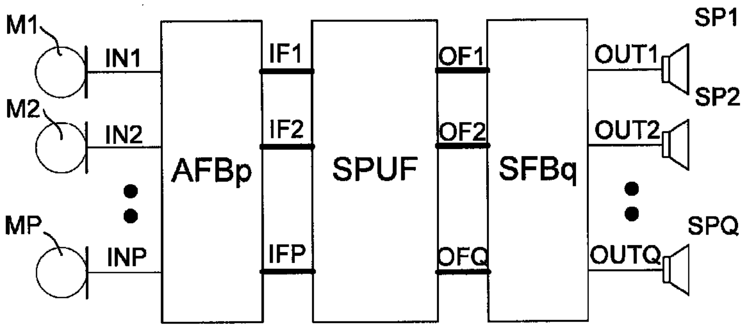

FIG. 2A and FIG. 2B show embodiments of an audio processing device according to the present disclosure comprising a multitude P of microphones (e.g. more than 1 microphone) M1, M 2, . . . , MP, and a multitude Q of output transducers (e.g. more than 1 loudspeaker) SP1, SP2, . . . , SPQ. The signal processing of the forward and analysis paths of the audio processing is symbolized by signal processing unit SPU in FIG. 2A. The signal processing unit SPU receives the P inputs IN1, IN2, . . . , INP from the P microphones and provides Q processed outputs OUT1, OUT2, . . . , OUTQ to respective of the Q loudspeakers. The processing of in the signal processing unit SPU may be performed fully or partially in the time domain or preferably at least partially in the frequency domain. In the embodiment of FIG. 2B the signal processing unit (SPU in FIG. 2A) comprises analysis filter bank unit AFBp, a signal processing unit SPUF, and a synthesis filter bank SFBq. The analysis filter bank unit AFBp is configured for splitting the P microphone signals IN1, IN2, . . . , INP in a number of frequency bands and providing band split microphone signals IF1, IF2, . . . , IFP, each representing a respective of the time domain input signals IN1, N2, . . . , INP in a number of frequency bands (as indicated by the bold connection between the AFBp and SPUF units (and between the SPUF and SFBq units). Correspondingly, the synthesis filter bank unit SFBp is configured for synthesizing the Q processed time-frequency domain output signals OF1, OF2, . . . , OFQ from the signal processing unit SPUF to respective (processed) time-domain output signals OUT1, OUT2, . . . , OUTQ to respective of the Q loudspeakers. The signal processing unit SPUF is thus configured to process and analyze the input signals in the frequency domain. Other embodiments of an audio processing device according to the present disclosure shown and described below contain one or two input transducers and only one output transducer. It is the intention that such embodiments may incorporate more than one or two input transducers and/or more than one output transducer, as the specific application requires.

Figure 2C:
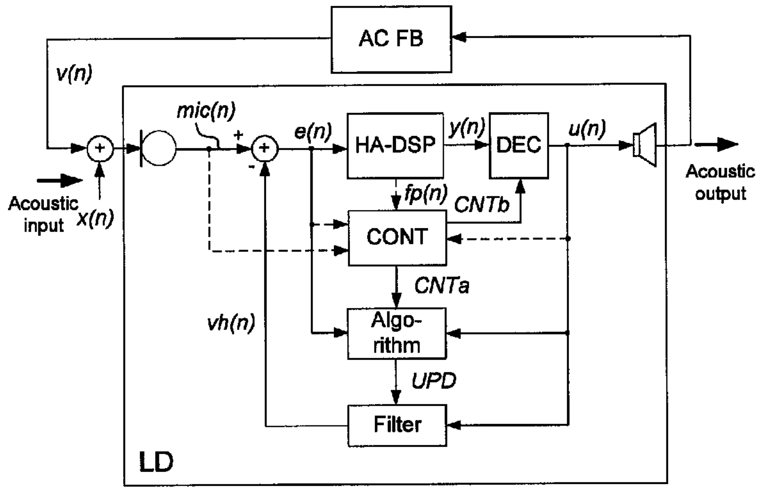

FIG. 2C shows an embodiment of an audio processing device, e.g. a listening device, e.g. a hearing instrument. The exemplary embodiment of FIG. 2C comprises the same elements as shown in and discussed in connection with FIG. 1C. Additionally, the forward path of the embodiment of FIG. 2C comprises a de-correlation unit (DEC) for decreasing correlation (increasing de-correlation) between the electric output signal u(n) fed to the speaker (and to the Algorithm and Filter parts of the adaptive filter for estimating feedback) and an electric input signal provided by the microphone. The de-correlation is important for the quality of the feedback estimate (in particular in case of the presence of significant amounts of tonal components in the (target) input signal). The quality of the feedback estimate provided by the adaptive algorithm based on input signals e(n) (error) and u(n) (reference), e.g. by determining filter coefficients that minimizes the energy content of the error signal, is higher the less correlated signals e(n) and u(n) are. In the embodiment of FIG. 2C, the de-correlation unit (DEC) is located in the forward path after the signal processing unit (HA-DSP) taking as input the processed output signal y(n) from the signal processing unit. Alternatively, the de-correlation unit may be located elsewhere in the forward path (or in the analysis path). On the input side, the (acoustic) target signal is termed x(n), and the feedback signal at the microphone is termed v(n). The combined (acoustic) signal x(n)+v(n) is picked up by the microphone and converted to electric input (or microphone) signal mic(n). The estimated feedback signal vh(n) from the adaptive filter is subtracted from the microphone signal mic (n) in sum unit '+' whose resulting output (error signal) e(n) is fed to the signal processing unit HA-DSP as well as to the algorithm part of the adaptive filter.

Various embodiments of de-correlation units are known from the prior art, e.g. as discussed in U.S. Pat. No. 5,748,751 or in [Joson et al., 1993].

The audio processing device further comprises control unit (CONT) for controlling the de-correlation unit (DEC), cf. control signal CNTb, and the adaptive algorithm (Algorithm) of the feedback estimation system (Algorithm, Filter), cf. control signal CNTa. The control unit (CONT) is e.g. configured to control the type of and/or amount of de-correlation applied to the signal and the adaptation rate of the adaptive algorithm (e.g. defined by the points in time where the feedback estimate is determined (and updated), cf. signal UPD). In the embodiment of FIG. 2C, the control unit (CONT) further comprises detectors for indicating the degree of correlation between the electric input signal (or a signal derived therefrom) and the electric output signal. Preferably, the control unit (CONT) comprises a correlation detection unit for determining the auto-correlation of a signal of the forward path and providing an AC-value. Auto-correlation of one or more signals of the forward path may be provided by the control unit, e.g. of the electric input signal, mic(n), of the feedback corrected input signal e(n), of a further processed version fp(n) taken from of the feedback corrected input signal e(n) (fp(n) being tapped from the signal processing unit HA-DSP), of the electric output signal u(n), etc. Alternatively or additionally, the control unit (CONT) comprises a correlation detection unit for determining cross-correlation between two different signals of the forward path and providing an XC-value. Cross-correlation values may e.g. be provided between signals selected from the group comprising mic(n), e(n), fp(n), y(n), and u(n) (cf. FIG. 2C). The control unit (CONT) may further comprise other detectors, e.g. a speech detector, a feedback detector, a tone detector, an audibility detector, a feedback change detector, etc. (cf. e.g. FIG. 6, 8). In an embodiment, the control unit (CONT) is configured to control the type (and amount) of de-correlation applied to a signal of the forward path by the de-correlation unit (DEC), e.g. frequency/phase modulation or amplitude modulation. Preferably, the audio processing device (e.g. the control unit CONT or the algorithm part Algorithm) comprises a memory for storing a number of previous estimates of the feedback path, in order to be able to rely on a previous estimate, if a current estimate is judged (e.g. by the control unit CONT) to be less optimal.

Figure 2D:
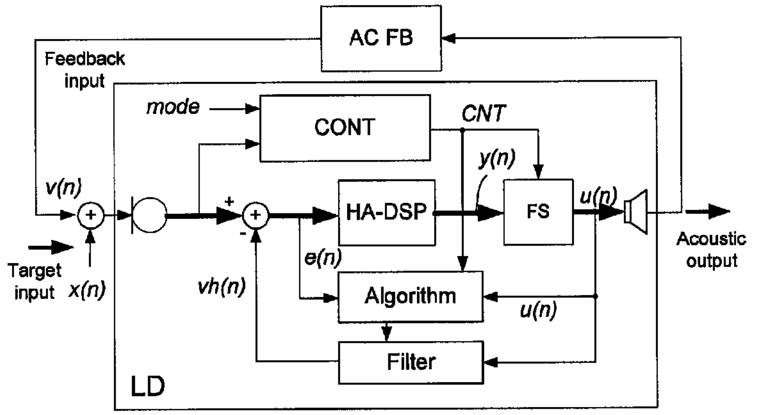

FIG. 2D shows an embodiment of an audio processing device comprising the same functional elements as shown in and discussed in connection with FIG. 2C. The interconnections of the forward path (here mic(n), e(n), y(n), and u(n)) are in FIG. 2D indicated by bold arrows connecting the functional components of the forward path (here a microphone unit, a SUM (or subtraction) unit ('+'), a signal processing unit (HA-DSP), a de-correlation unit (FS), and a loudspeaker (receiver) unit). In the embodiment of FIG. 2D, the de-correlation unit (DEC in FIG. 2C) is a frequency compression unit (FS) for applying a frequency shift Δf to the processed output of the signal processing unit (HA-DSP). Preferably the frequency shift is relatively small (preferably sufficiently small to be inaudible, at least in some modes of operation of the audio processing device or in some acoustic environments). Preferably the frequency shift is small relative to the width of the frequency range of operation of the device (e.g. 20 Hz to 8 kHz) or to a sampling frequency (e.g. 20 kHz) of the device, relatively small meaning e.g. smaller than or equal to a predefined amount, e.g. 3 per mille. Further, the control unit (CONT) comprises a mode input for selecting a particular mode of operation of the audio processing device. Such mode may be selectable via a user interface and/or be automatically determined from a number of detector inputs (e.g. from one or more of an auto-correlation detector, a cross-correlation detector, a feedback detector, a voice detector, a tone detector, a feedback change detector, an audibility detector, etc.). The mode input may influence or form basis of control output(s) CNT from the control unit for controlling the de-correlation unit (FS) and/or the adaptive algorithm of the feedback estimation system.

Figure 2E:
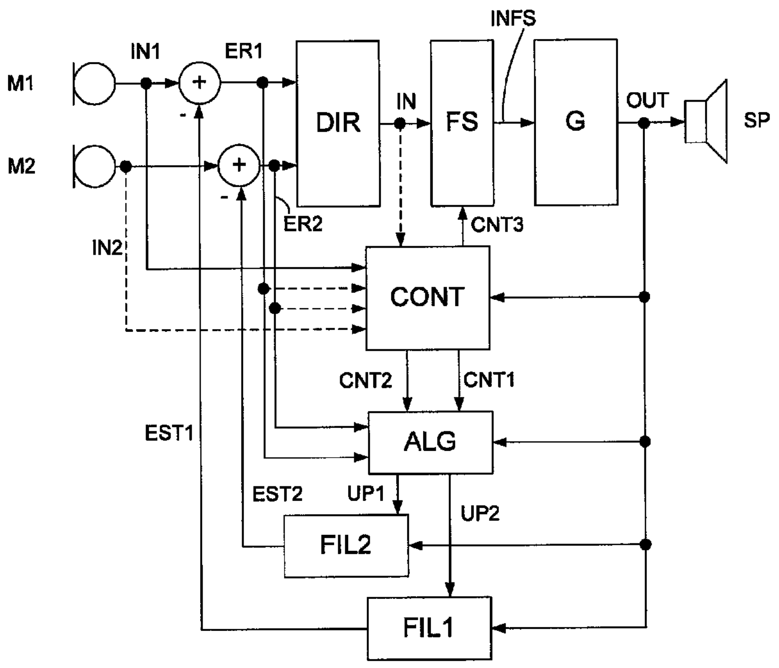

FIG. 2E shows an embodiment of an audio processing device comprising the same functional elements as shown in and discussed in connection with FIG. 2C. Additionally, the audio processing device comprises a microphone system comprising two microphone units (M1, M2) and a directional algorithm (DIR), whereby different feedback paths from the speaker SP to each of the microphones M1, M2 exists. Correspondingly, the audio processing device comprises two feedback cancellation systems, one for each feedback path (microphone). Each feedback cancellation system comprises an adaptive filter ((ALG, FIL1), (ALG, FIL2), respectively) for providing an estimate (EST1, EST2, respectively) of the feedback path in question, and a summation (subtraction) unit for subtracting the feedback estimate (EST1, EST2, respectively) from the microphone input signal (IN1, IN2, respectively) and providing a feedback corrected (error) signal (ER1, ER2, respectively). The error signals (ER1, ER2) are fed to the directional algorithm (DIR) and to the (common) algorithm part (ALG) of the adaptive filters. The directional block (DIR) provides as an output a resulting (feedback corrected) input signal IN in the form of a weighted combination of the input signals (ER1, ER2). The forward path further comprises de-correlation unit (FS) for applying a frequency shift to the input signal IN and a signal processing unit (G) for applying a resulting (frequency dependent) gain to the signal INFS from the de-correlation unit. The processed output OUT of the signal processing unit (G) is fed to the speaker unit (SP) and to the adaptive filters of the feedback estimation units. Compared to the embodiments of FIG. 2C, 2B, the order of the de-correlation unit (DEC, FS, respectively) and the signal processing unit (G, HA-DSP, respectively) is reversed. The control unit (CONT) receives inputs from the 'output side' (output signal OUT) and from the 'input side' (microphone input IN1) of the forward path, and optionally receives one or more of signals IN2, ER1, ER2, IN, e.g. to calculate auto-correlation of and/or cross-correlation between signals of the forward path, or to derive other characteristics (e.g. parameters or properties) of the signals. The control unit (CONT) provides control outputs CNT1, CNT2 to control the algorithm part (ALG) of the adaptive filters, and CNT3 to control the de-correlation unit (FS). The algorithm part (ALG) is preferably configured to calculate independent filter coefficients (UP1, UP2) for the two variable filters (FIL1, FIL2). In an embodiment, the control of the two adaptive filters is independent. Alternatively, the same control parameters may be used (e.g. same adaptation rate, simultaneous change of adaptation rate, etc.).

In the embodiment of FIG. 2E, signal processing in the forward path and analysis path may be performed in the time domain or in the frequency domain.

Figure 2F:
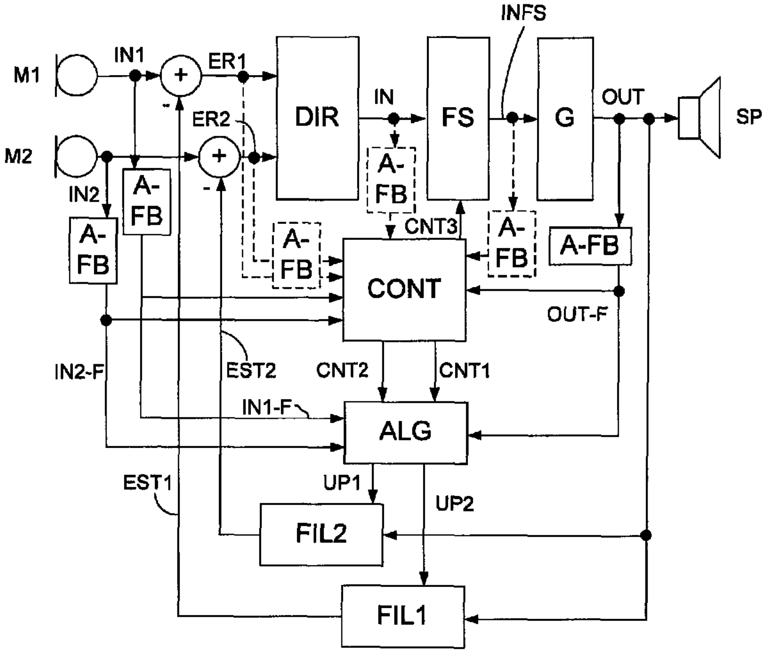

FIG. 2F shows an embodiment of an audio processing device comprising the same functional elements as shown in and discussed in connection with FIG. 2D. In the embodiment of FIG. 2F, signal processing in the analysis path (feedback estimation, etc.) is performed fully or partially in the frequency domain, cf. analysis filter banks A-FB, and signals IN1-F, IN2-F, OUT-F indicating 'frequency domain'). In the embodiment of FIG. 2F, the analysis path comprising the feedback estimation system (ALG, FIL1, FIL2) and a control unit (CONT), of which a cross-correlation and/or an auto-correlation detector (and other detectors, e.g. a feedback detection unit) form part, is operated fully or partially in the frequency domain. Analysis filter banks (A-FB) are inserted in the microphone signal paths to provide the signals IN1, IN2 (or alternatively or additionally the signals ER1, ER2) in a number of frequency bands in an analysis path (cf. signals IN1-F, IN2-F ('-F' indicating 'frequency domain')). In such case an analysis filter bank is likewise inserted in the output part of the analysis path to provide signal OUT in a number of frequency bands (signal(s) OUT-F). The signals of the forward path, on the other hand, comprising directional (DIR), de-correlation (FS) and gain (G) blocks are time domain signals.

Alternatively, the forward path from the input transducer (M1, M2) to the output transducer (SP) and comprising the gain block (G) as well as the analysis path comprising the feedback estimation system (ALG, FIL1, FIL2) and control unit (CONT) are operated in the frequency domain. Alternatively any other split between operation in the time domain and frequency domain may be used depending on the particular application in question.

FIGS. 3A-3B through 5A-5C illustrate a number of exemplary schemes for controlling de-correlation (here frequency shift) and/or adaptation rate depending on a value of auto-correlation and/or cross-correlation of signals of the forward path. The scales on either axis of FIGS. 3A-3B through 5A-5C are not necessarily linear. The auto-correlation and/or cross-correlation values may be normalized or un-normalized. The range of depicted AC- or XC-values may be the full range or only a part of the possible values. If normalized, values AC- and XC-values fall between −1 and +1. FIGS. 3A-3B through 5A-5C may be interpreted to illustrate normalized, absolute values of auto-correlation and/or cross-correlation assuming values between 0 (towards the left) representing little (0=no) correlation and 1 (towards the right) representing strong (1=perfect) correlation. In an embodiment, the leftmost and rightmost values of AC (or XC) are intended to be 0 and 1, respectively. It is generally assumed that (for a given drawing) the larger the subscripts, the numerically larger the AC- or XC-values, e.g. $AC_{3\text{-}FS} > AC_{2\text{-}FS}$.

Figure 3A:
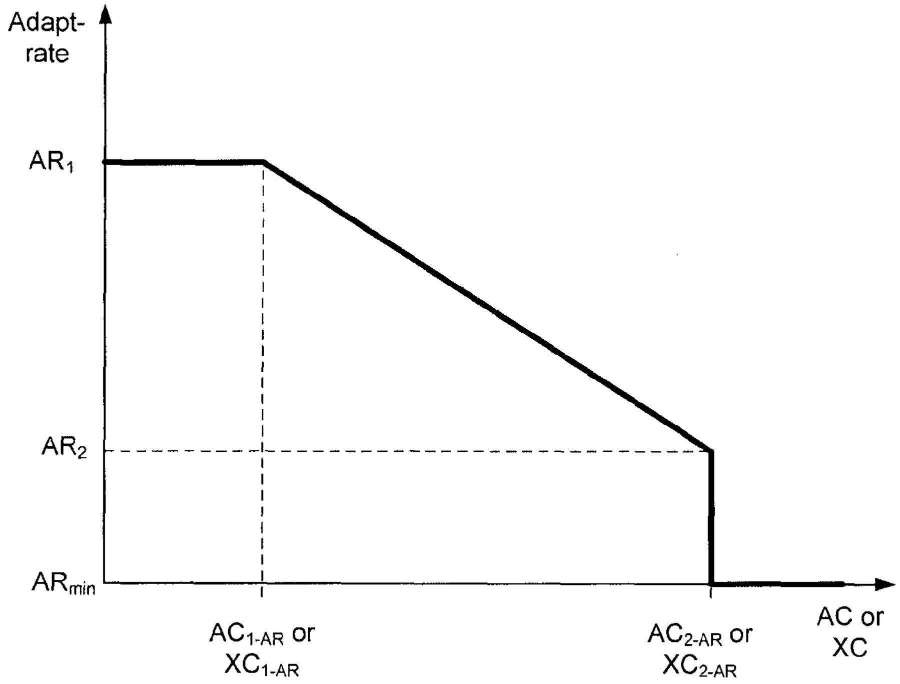
FIGS. 3A-3B show two schematic examples of the relationship between adaptation rate for an adaptive algorithm of the feedback estimation system and auto-correlation or cross-correlation of signals of the forward path of the audio processing device.
Figure 3B:
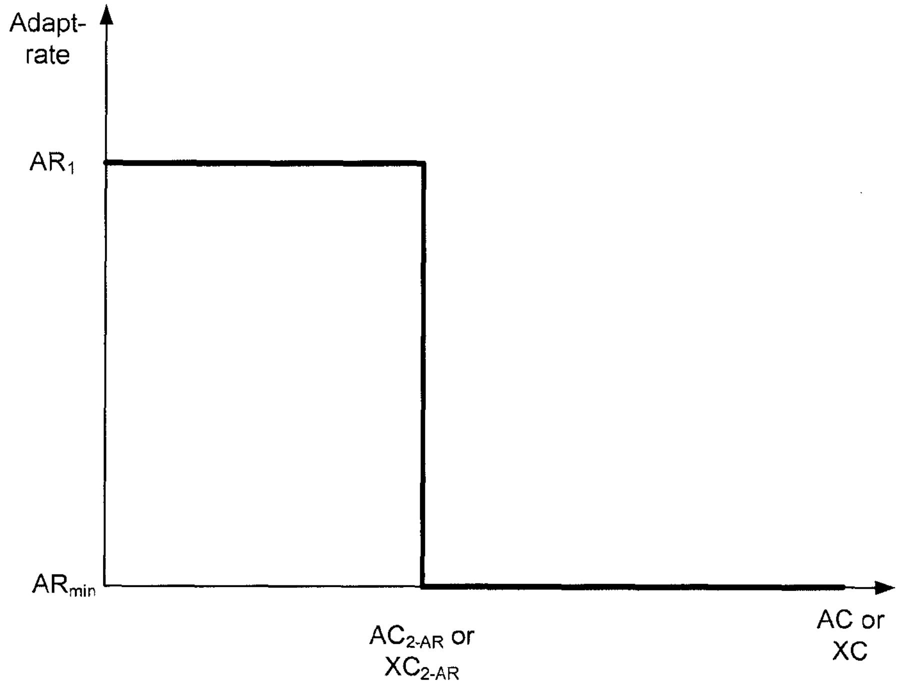

FIGS. 3A-3B show two schematic examples of the relationship between adaptation rate for an adaptive algorithm of the feedback estimation system and auto-correlation or cross-correlation of signals of the forward path of the audio processing device.

In the scheme of FIG. 3A the adaptation rate is equal to a fixed value (here $AR=AR_1$) for AC- or XC-values below a threshold value $AC_{1\text{-}AR}$ or $XC_{1\text{-}AR}$, respectively. A gradual change from the fixed relatively high value of adaptation rate ($AR=AR_1$) to a lower rate ($AR=AR_2$) occurs for AC- or XC-values in the range $AC_{1\text{-}AR} \le AC \le AC_{2\text{-}AR}$ or $XC_{1\text{-}AR} \le XC \le XC_{2\text{-}AR}$, respectively. When the AC- or XC-values reach $AC_{2\text{-}AR}$ or $XC_{2\text{-}AR}$, respectively, the adaptation rate may be kept at the relatively lower value or (as illustrated here) abruptly decreased to a minimum value $AR=AR_{min}$ (e.g. $AR_{min}=0$, so that no update of the feedback estimate is performed) and remains constant at this value for AC- or XC-values larger than $AC_{2\text{-}AR}$ and $XC_{2\text{-}AR}$, respectively. In an embodiment, $AR_2=AR_{min}$ (e.g. $AR_{min}=0$).

FIG. 3B illustrates a simpler scheme than FIG. 3A, where two modes of operation are assumed, a first mode where the adaptive algorithm is updated with a first fixed adaptation rate ($AR=AR_1$) for AC- or XC-values smaller than $AC_{2\text{-}AR}$ and $XC_{2\text{-}AR}$, respectively, and a second mode where the adaptation rate is fixed to a second fixed adaptation rate ($AR=AR_{min}$, e.g. $AR_{min}=0$, so that no update of the feedback estimate is performed) for AC- or XC-values larger than $AC_{2\text{-}AR}$ and $XC_{2\text{-}AR}$, respectively.

Figure 4A:
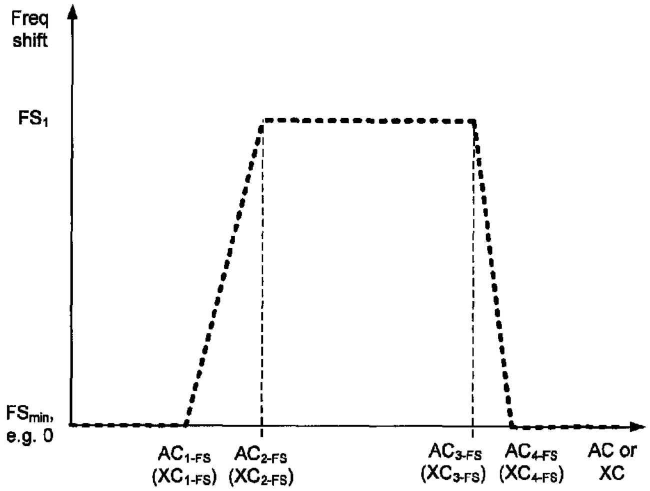
FIGS. 4A-4B show two schematic examples of the relationship between size of frequency shift applied to a signal of the forward path to reduce the risk of howl and auto-correlation or cross-correlation of signals of the forward path of the audio processing device.
Figure 4B:
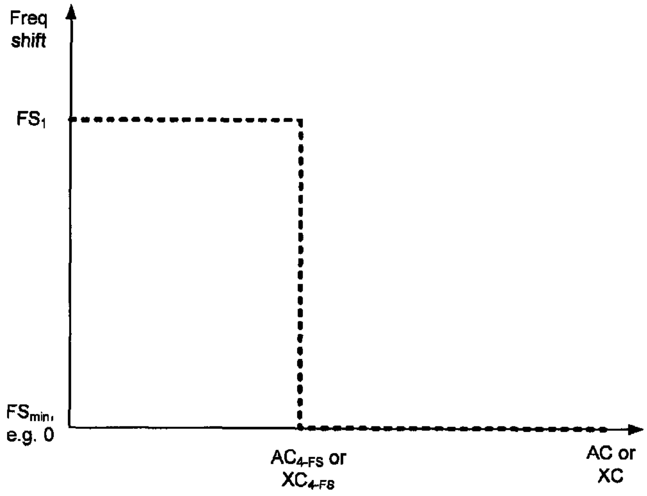

FIGS. 4A-4B show two schematic examples of the relationship between size of frequency shift applied to a signal of the forward path to reduce the risk of howl and auto-correlation or cross-correlation of signals of the forward path of the audio processing device. For a given frequency shift applied to a signal of the forward path, a value of auto-correlation or cross-correlation in a signal of the forward path may be taken as an indicator of the risk of audibility of the artefacts introduced into the signal by the application of the frequency shift.

In the scheme of FIG. 4A the frequency shift Δf is equal to its minimum value (here Δf=FS=0) for AC- or XC-values below a threshold value $AC_{1\text{-}FS}$ or $XC_{1\text{-}FS}$, respectively, a gradual change from no frequency shift ($\Delta f=FS=0$) to frequency shift ($\Delta f=FS=FS_1$) occurs for AC- or XC-values in the range $AC_{1\text{-}FS}\leq AC\leq AC_{2\text{-}FS}$ or $XC_{1\text{-}FS}\leq XC\leq XC_{2\text{-}FS}$, respectively. In the range of AC- or XC-values $AC_{2\text{-}FS}\leq AC\leq AC_{3\text{-}FS}$ or $XC_{2\text{-}FS}\leq XC\leq XC_{3\text{-}FS}$, respectively, the frequency shift remains constant (at $\Delta f=FS=FS_1$). The frequency shift is gradually decreased back to its minimum values (here 0) for AC- or XC-values between $AC_{3\text{-}FS}$ and $AC_{4\text{-}FS}$, or between $XC_{3\text{-}FS}$ and $XC_{4\text{-}FS}$, respectively. For AC- or XC-values larger than $AC_{4\text{-}FS}$ and $XC_{4\text{-}FS}$, respectively, the frequency shift remains at its minimum values (here 0, i.e. no frequency shift is applied to the output signal).

FIG. 4B illustrates a simpler scheme than FIG. 4A, where two modes of operation are assumed, a first mode where frequency shift is applied ($\Delta f=FS=FS_1$) for AC- or XC-values smaller than $AC_{4\text{-}FS}$ and $XC_{4\text{-}FS}$, respectively, and a second mode where no frequency shift is applied ($\Delta f=FS=0$) for AC- or XC-values larger than $AC_{4\text{-}FS}$ and $XC_{4\text{-}FS}$, respectively.

Figure 5A:
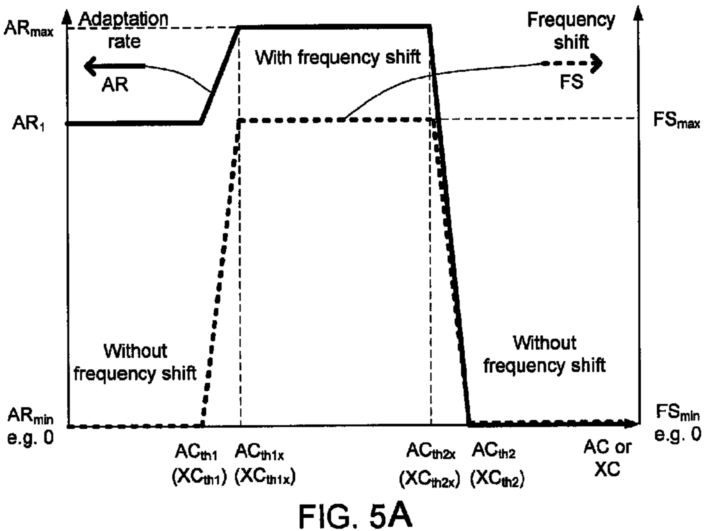
FIGS. 5A-5C show three schematic examples of the relationship between, respectively, size of frequency shift applied to a signal of the forward path to reduce the risk of howl and adaptation rate for an adaptive algorithm of the feedback estimation system, and auto-correlation or cross-correlation of signals of the forward path of the audio processing device.
Figure 5B:
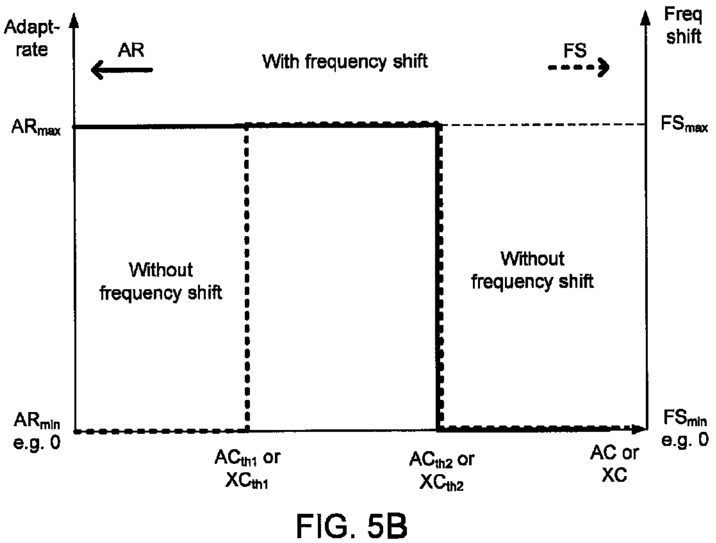
Figure 5C:
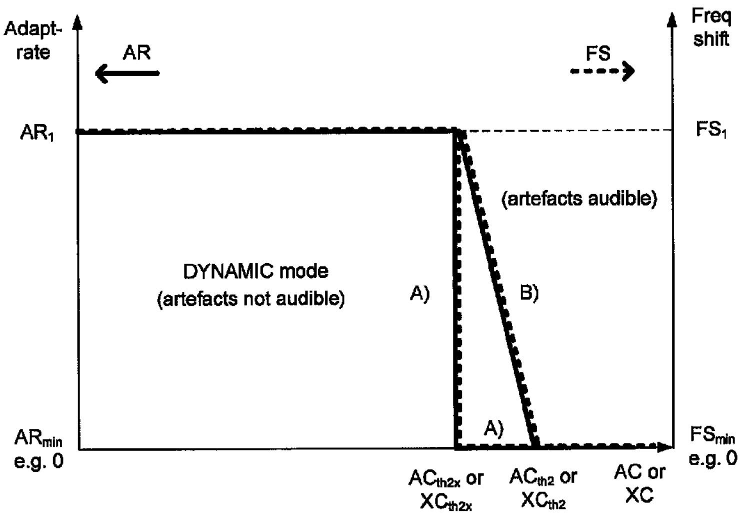

FIGS. 5A-5C show three schematic examples of the relationship between, respectively, size of frequency shift applied to a signal of the forward path to reduce the risk of howl and adaptation rate for an adaptive algorithm of the feedback estimation system, and auto-correlation or cross-correlation of signals of the forward path of the audio processing device. FIG. 5A is a more general scheme than FIGS. 5B and 5C. FIG. 5B is described first.

FIG. 5B schematically illustrates a specific example of various modes of operation of an audio processing device, e.g. a hearing instrument, wherein the different modes of operation are influenced, such as controlled, by a value of auto-correlation AC of a signal of the forward path and/or by a value of cross-correlation XC of two different signals of the forward path. In the example of FIG. 5B, three different modes of operation of the device are illustrated, a first mode corresponding to relatively low values of auto-correlation ($AC\leq AC_{th1}$) or cross-correlation ($XC\leq XC_{th1}$) (relatively low risk of audibility of artefacts), a second mode corresponding to medium values of auto-correlation ($AC_{th1}<AC\leq AC_{th2}$) or cross-correlation ($XC_{th1}<XC\leq XC_{th2}$) (medium (acceptable) risk of audibility of artefacts), and a third mode corresponding to relatively high values of auto-correlation ($AC>AC_{th2}$) or cross-correlation ($XC>XC_{th2}$) (relatively (inacceptable) high risk of audibility of artefacts).

In the first mode (at relatively low AC-/XC-values), the control unit is configured to provide that the de-correlation unit is inactive (e.g. providing that no frequency shift FS is applied to a signal of the forward path, $\Delta f=FS=0$) AND to allow the adaptive algorithm to adapt the feedback estimate according to a normal scheme, e.g. at a normal rate (e.g. a predefined fixed rate, here $AR=AR_{max}$)), when the AC-values (and/or the XC-values) are below a predefined first threshold value ($AC_{th1}$, $XC_{th1}$). The predefined threshold value ($AC_{th1}$, $XC_{th1}$) is determined as a compromise between an acceptable precision or reliability of the feedback estimate (in the face of increasing tonal components) while avoiding the inconveniences of applied de-correlation (e.g. frequency shift, which may create audible artefacts).

In the second mode (at intermediate AC-/XC-values), the control unit is configured to provide that the de-correlation unit is active (e.g. providing that a predefined frequency shift, here $\Delta f=FS=FS_{max}$, is applied to a signal of the forward path) AND to allow the adaptive algorithm to adapt the feedback estimate according to a normal scheme, e.g. at a normal rate (e.g. a predefined fixed rate, here $AR=AR_{max}$) when the AC-values (and/or the XC-values) are in a range between the predefined first threshold value ($AC_{th1}$, $XC_{th1}$) and a second predefined threshold value ($AC_{th2}$, $XC_{th2}$). The predefined threshold value ($AC_{th2}$, $XC_{th2}$) is determined by an acceptable level of audible artefacts introduced by the applied de-correlation (e.g. frequency shift).

In the third mode (at relatively high AC-/XC-values), the control unit is configured to provide that the de-correlation unit is inactive (e.g. providing that no frequency shift is applied, $\Delta f=FS=0$), AND the adaptive algorithm is halted (i.e. the adaptation rate is set equal to zero, $AR=0$) when the AC-values (and/or the XC-values) are larger than the second predefined threshold value ($AC_{th2}$, $XC_{th2}$).

FIG. 5B represents an example of a more specific scheme than FIG. 5A.

The scheme of FIG. 5A is equal to the scheme of FIG. 5B, if $AR_1=AR_{max}$, $AC_{th1}=AC_{th1x}$ and $AC_{th2}=AC_{th2x}$). A difference to FIG. 5B is that the shift from no frequency shift ($\Delta f=FS=0$) to frequency shift ($\Delta f=FS=FS_{max}$) is gradual and occurs for AC- or XC-values between $AC_{th1}$ and $AC_{th1x}$, or between $XC_{th1}$ and $XC_{th1x}$, respectively. In the same range of AC- or XC-values, the adaptation rate of the adaptive algorithm increases from its initial value $AR=AR_1$ at relatively low AC- or XC-values ($\leq AC_{th1}$ or $XC_{th1}$) to $AR=AR_{max}$. for $AC\geq AC_{th1x}$ (or $XC\geq XC_{th1x}$). Likewise in FIG. 5A, the frequency shift and the adaptation rate are gradually decreased to their minimum values (here 0) for AC- or XC-values between $AC_{th2x}$ and $AC_{th2}$, or between $XC_{th2x}$ and $XC_{th2}$, respectively. In the range of AC- or XC-values $AC_{th1x}\leq AC\leq AC_{th2x}$ or $XC_{th1x}\leq XC\leq XC_{th2x}$, respectively, the frequency shift and adaptation rate remain constant (at $\Delta f=FS=FS_{max}$ and $AR=AR_{max}$, respectively). For AC- or XC-values larger than $AC_{th2}$ and $XC_{th2}$, respectively, frequency shift and adaptation rate remain at their minimum values (here 0, i.e. no frequency shift is applied and no update of feedback estimates is performed).

FIG. 5C shows a further embodiment of a scheme for controlling frequency shift and adaptation rate depending on the audibility of artefacts introduced by the frequency shift (as indicated by the auto-correlation or cross-correlation value). In the scheme of FIG. 5C, a constant frequency shift $FS=FS_1$ is applied, and an update of the feedback estimate is performed at a constant adaptation rate of $AR=AR_1$ for auto-correlation (or cross-correlation) values below a predefined threshold value $AC_{th2x}$ (or $XC_{th2x}$), where artefacts introduced by the frequency shift are in-audible (or audible to an acceptable level). Such behaviour may e.g. represent a DYNAMIC mode of operation as described in Examples 1 and 2 below (no feedback, no speech or music, no audible artefacts). For AC (or XC) values larger than the threshold value $AC_{th2x}$ (or $XC_{th2x}$), frequency shift and adaptation rate are either abruptly reduced to minimum values $FS_{min}$ and $AR_{min}$, respectively, as in path A), or gradually as in path B). In an embodiment, at least one of the minimum values is equal to zero. In an embodiment, one of frequency shift and adaptation rate is abruptly reduced to a minimum value, while the other is reduced gradually for AC- (or XC-) values beyond $AC_{th2x}$ (or $XC_{th2x}$). In an embodiment, one of frequency shift and adaptation rate is reduced to a minimum value equal to zero, while the other is reduced to a minimum value different from zero.

In FIGS. 5A and 5C, the gradual changes of adaptation rate and frequency shift are shown to be linear. This need not be the case but may be optimized to the application in question. Further, the shifts in adaptation rate and frequency shift are shown to occur at the same threshold values (e.g. $AC_{th1}$, $AC_{th2}$). This need not be the case either, although a certain predefined relationship is referred. The same is the case for the schemes shown in FIGS. 3A and 4A. Finally, the schemes shown are only examples. Other schemes are possible.

Figure 6:
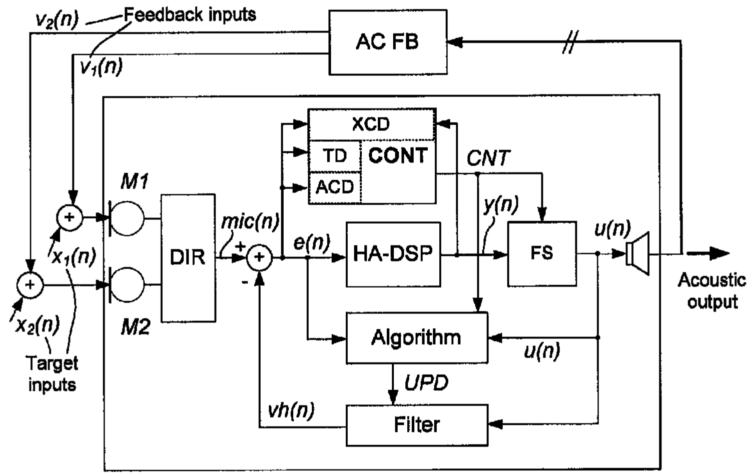
FIG. 6 shows a further embodiment of an audio processing device according to the present disclosure.

FIG. 6 shows an embodiment of an audio processing device, e.g. a listening device such as a hearing instrument, comprising the same functional elements as shown in and discussed in connection with FIG. 2C. In FIG. 6, the control unit (CONT) comprises a cross-correlation detector (XCD), an auto-correlation detector (ACD), and a feedback tone detector (TD) thereby allowing an improved control of the feedback estimation system.

Preferably, the signal(s) from the input side of the audio processing device, which form part of the calculation of auto-correlation and/or cross-correlation, is(are) based on a target input signal (exclusive of a possible feedback component, e.g. signal e(n) in FIG. 6). The signal from the input side used in the correlation determination may alternatively be the (or one of the) microphone signal(s), or it may be a directional signal (e.g. signal mic(n) in FIG. 6).

In the embodiment of FIG. 6, the auto-correlation detector (ACD) estimates auto-correlation of the feedback corrected input (error) signal e(n) and provides an AC-value at regular points in time as a current measure thereof. The cross-correlation detector (XCD) estimates cross-correlation between feedback corrected error signal e(n) and a processed output signal y(n) from the signal processing unit (HA-DSP) and provides an XC-value at regular points in time as a current measure thereof. The feedback tone detector (TD) (or howl detector) is configured to identify tonal components in the electric input signal (e.g. mic(n), or, as here, in the feedback corrected input (error) signal e(n)).

Compared to the embodiment of FIG. 2C, the audio processing device of FIG. 6 comprises two input transducers (microphones M1, M2) forming a directional microphone system together with directional algorithm block (DIR) and providing a resulting (directional, or omni-directional) microphone signal mic(n). The microphones (M1, M2) each pick up a time varying combination signal comprising a target part ($x_1$(n), $x_2$(n) and a feedback part ($v_1$(n), $v_2$(n)). The output mic(n) of directional block DIR (the resulting electric input signal) is a weighted combination (e.g. a weighted sum) of the individual electric (digitized) signals from the two microphones (M1, M2).

The cross correlation of two digitized signals u[n] and y[n] is defined by the following formula:

$$(u^{*}y)[n] = \sum_{m=-\infty}^{\infty} u^{*}[m]\cdot y[n+m]$$

where u* denotes the complex conjugate of u. When normalized (by subtracting respective mean values $\mu_u$ and $\mu_y$ from the signal expressions and dividing by a product of the respective standard variations $\sigma_u$, $\sigma_y$ of the signal values), values of the resulting cross-correlation coefficient lie in the interval from −1 to +1 where values close to 0 indicate little correlation and values close to −1, or +1 indicate strong correlation.

The auto-correlation of a digitized signal x[n] at lag j is defined by the following formula:

$$R_{xx}[j] = \sum_{n=-\infty}^{\infty} x[n]\cdot x^{*}[n-j]$$

where x* denotes the complex conjugate of x. When normalized (by subtracting a mean value μ from the signal expressions and dividing by the variance σ of the signal values), values of the resulting auto-correlation coefficient lie in the interval from −1 to +1, where values close to 0 indicate little correlation and values close to −1, or +1 indicate strong correlation.

In case the forward path is operated in the time domain, the signals (e.g. speech signals) are real (non-complex) and the above formulae (or equivalent formulae expressed as integrals) can be written without complex conjugation (because x=x*, if x is real).

An appropriate estimate of either parameter is typically sufficient to achieve acceptable results. The number of values of n and m needed in the summations may e.g. be limited. Alternatively, other approximations providing estimates of cross-correlation and auto-correlation, respectively, may be implemented and used.

In the embodiment of FIG. 6, analogue to digital converters are e.g. included in microphone units M1, M2. Signal x[n] in the above formula for auto-correlation can be any signal of the forward path, but is shown to be the feedback corrected input signal (error signal e(n)). Correspondingly, signal y[n] in the above formula for cross-correlation may e.g. be represented in FIG. 6 by resulting (directional) microphone signal mic(n) or (as shown) by the feedback compensated (error) signal e(n) or filtered versions of one of these signals. Signal u[n] in the formula for cross-correlation may e.g. be represented in FIG. 6 by output signal u(n), or (as shown) by the processed output signal y(n) of the signal processing unit (HA-DSP) or a filtered version thereof.

The tone detector TD is adapted to detect tonal components of the input signal (here error signal e(n)). The control unit CONT is preferably configured to—upon detection of a tonal input—detect whether the tonal input has its origin in a feedback signal ($v_1$(n) or $v_2$(n) in FIG. 6) or is part of an external input (target) signal ($x_1$(n) or $x_2$(n) in FIG. 6), thereby implementing a feedback detector. This can e.g. be done by making a modification (e.g. a phase change) to the tonal component, propagate the modified signal via the output transducer. If the modification can be detected by the control unit (after having been picked up by the microphone system, it must have been propagated by the external feedback path (AC FB in FIG. 6), in which case it can be concluded that the tonal component is due to feedback. If not, it can be concluded that the tonal component is from an external signal. Such tone or howl detection unit may in general be of any known kind (an example is described in EP 1 718 110 A1).

In an embodiment, the cross-correlation detector (XCD) comprises a variable delay unit adapted to vary the mutual delay between the signals used as inputs to the cross-correlation unit. In an embodiment, the mutual delay between the signals is varied until a maximum cross-correlation is achieved. In an embodiment, the delay variation and optimization of cross-correlation is performed according to a predefined scheme, e.g. periodically.

The determination of cross-correlation and/or auto-correlation may in practice e.g. be performed in a signal processing unit (HA-DSP) of the audio processing device, where also the directionality and/or the gain (and possible other audio processing algorithms, e.g. noise reduction) are determined. Similarly, the delay variation and optimization of cross-correlation may preferably be performed in the signal processing unit.

The determination of auto-correlation and cross-correlation of signals in a hearing aid (to identify wind noise) is e.g.

described in EP 1148016 A1. An autocorrelation estimator is e.g. described in US 2009/028367 A1.

The control unit (CONT) is preferably configured to control the adaptive algorithm of the adaptive filter(s) of the feedback estimation system. Preferably the adaptation rate of the adaptive filter(s) (e.g. Algorithm in FIG. 6) is/are controlled in dependence of the estimated auto-correlation or cross-correlation. In an embodiment, the adaptation rate AR follows—in particular modes—a scheme as outlined in FIG. 3, 5 or 7 or as described in Examples 1 and 2 below.

The control unit (CONT) is preferably configured to control the de-correlation unit (FS) for applying a frequency shift Δf to the output signal u(n). In an embodiment, the application of and/or the amount of frequency shift applied is/are controlled in dependence of the estimated auto-correlation or cross-correlation. In an embodiment, the application of frequency shift FS follows—in particular modes—a scheme as outlined in FIG. 4, 5 or 7 or as described in Examples 1 and 2 below.

In an embodiment, a scheme for controlling the application of frequency shift Δf to the output signal u(n), and adaptation rate AR of the adaptive algorithm (e.g. Algorithm in FIG. 6) depending on current detected auto-correlation or cross-correlation values is illustrated in FIG. 5.

EXAMPLE 1

Figure 7:
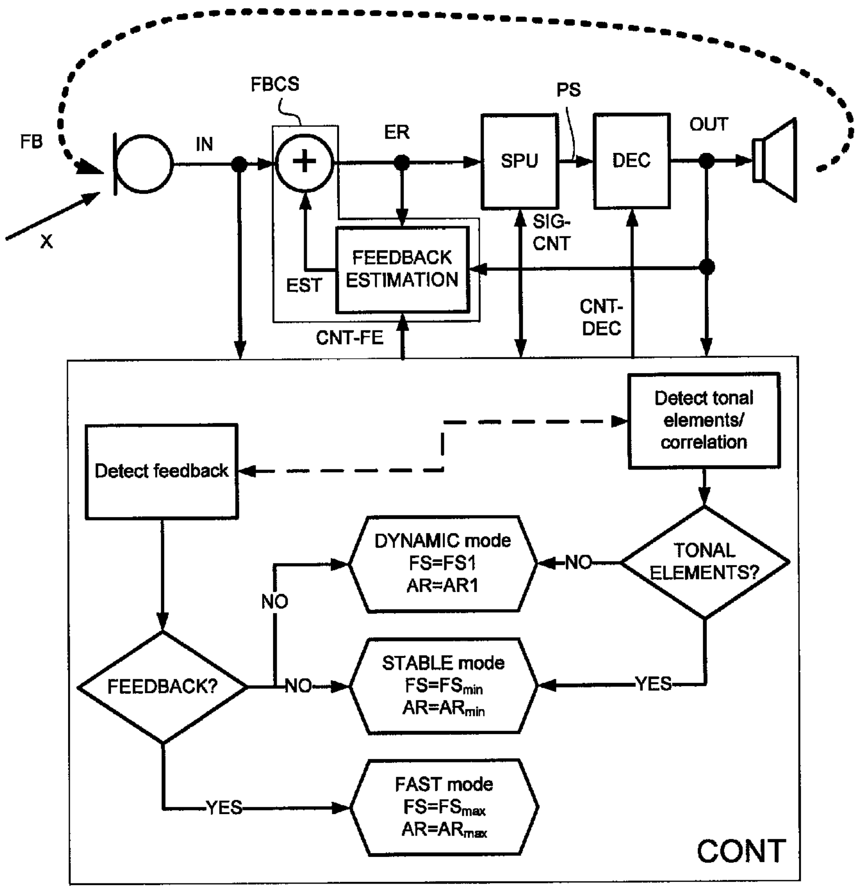
FIG. 7 shows an embodiment of a method and device for controlling an update algorithm of an adaptive feedback estimation system.

FIG. 7 illustrates an embodiment of a method of and device for controlling an update algorithm and a de-correlation unit of an adaptive feedback estimation system. FIG. 7 schematically illustrates a forward path of a listening device, the forward path comprising a microphone unit for picking up an input sound (FB+x) and providing an electric input signal IN, a combination unit ('+') for subtracting two input signals (IN−EST) and providing a resulting (error) signal (ER), a signal processing unit (SPU) for processing the resulting signal ER and providing a processed signal (PS), a de-correlation unit (DEC) for (in specific modes of operation) applying de-correlation (e.g. a constant frequency shift) to the processed signal PS and providing a processed (and possibly de-correlated) output signal OUT, and a speaker unit for providing an output sound based on the electric output signal OUT. The audio processing device further comprises a feedback estimation unit (FEEDBACK ESTIMATION) and a control unit (CONT). The two units form part of an analysis path for providing a an estimate EST of the feedback path from speaker unit to microphone unit (both included) based on input signals. OUT and ER and controlled by control signal CNT-FE from the control unit CONT. The control unit is configured to control an adaptive algorithm (e.g. its update rate) of the feedback estimation unit (control signal CNT-FE) and to control the de-correlation unit (e.g. the amount of de-correlation, e.g. frequency shift, via control signal CNT-DEC). The control unit (CONT) can further be configured to control a processing algorithm applied to a signal of the forward path in the signal processing unit (SPU). The analysis path is configured to analyse one or more signals of the forward path, here (at least) electric input signal IN and electric output signal OUT. Further, signals (e.g. a processed signal of the forward path and/or a signal derived therefrom, e.g. a detector signal) may be provided to the analysis path from the signal processing unit (SPU), cf. double arrow on signal SIG-CNT. The analysis path (here control unit CONT) comprises a feedback detector and a detector of tonal elements (e.g. an auto-correlation or cross-correlation detector). Its function is described in the following in terms of processes 'Detect tonal elements/correlation' and 'Detect feedback' and modes 'Stable mode', 'Dynamic mode' and 'Fast mode'.

Detect tonal elements/correlation: The sound environment is constantly monitored and it is decided which mode to apply in a given sound environment. If tonal components representative of speech and/or music are present (but no feedback), the risk of producing disturbing artefacts may be deemed too great and Stable Mode is preferred. In Stable mode, the update rate of the adaptive algorithm is decreased to $AR_{min}$ and preferably stopped ($AR_{min}$=0) and a previous set of parameters is used to estimate the feedback path. Likewise, the frequency shift FS is decreased to a minimum value ($FS_{min}$), preferably to zero ($FS_{min}$=0). In more dynamic environments comprising noise and complex sounds (not assumed to represent speech or music), the risk of producing artefacts should also be considered, and Dynamic Mode is prescribed. In Dynamic mode, the adaptive algorithm is regularly updated, and the update rate is in a normal (predefined) range ($AR_1$). Likewise, de-correlation is applied to a signal of the forward path, and the frequency shift FS is set to a normal (predefined) value ($FS_1$).

Detect feedback: A howl detector recognizes feedback or feedback-like signals in the input and takes appropriate action according to the nature of these. Internally generated feedback is promptly suppressed by shifting into Fast Mode where the inversion signal is updated with a relatively fast adaptation rate ($AR_{max}$) to cancel the feedback, and frequency shifting is applied with a relatively high (e.g. maximum) frequency shift ($FS_{max}$) to keep the system less sensitive to tonal input. In an embodiment, $AR_{max}$ is larger than or equal to $AR_1$. In an embodiment, $FS_{max}$ is larger than or equal to $FS_1$. The feedback detector may receive inputs from the detector of tonal components (correlation) as indicated by the dashed double arrowed line.

These decisions to enter a prescribed mode are arranged to happen within milliseconds allowing the system to choose optimal settings for preservation of great sound fidelity. The system is preferably configured to provide seamless and unnoticeable shifts between modes of operation and to provide a fast reaction to current problems.

The prescription of modes outlined above and in FIG. 7 can be summarized by the table below:

| Tonal elements | Feedback | Mode (FS,AR) |
|---|---|---|
| Yes | Yes | FAST ($FS_{max}$,$AR_{max}$) |
| Yes | No | STABLE ($FS_{min}$,$AR_{min}$) |
| No | No | DYNAMIC ($FS_1$,$AR_1$) |
| No | Yes | FAST ($FS_{max}$,$AR_{max}$) |

Thus, the described embodiment of a method according to the present application comprises three modes: DYNAMIC MODE—where updates to the feedback path (providing optimized preciseness of the inverted cancellation signal) are supported by frequency shift that de-sensitizes the system to tonal input. STABLE MODE—where feedback cancellation and feedback limit estimations ensure that feedback is suppressed and optimum gain is provided at all times. FAST MODE—where frequency shift allows a very fast update of the feedback path and makes sure that the audio processing device is resistant to "new" feedback.

EXAMPLE 2

Figure 8:
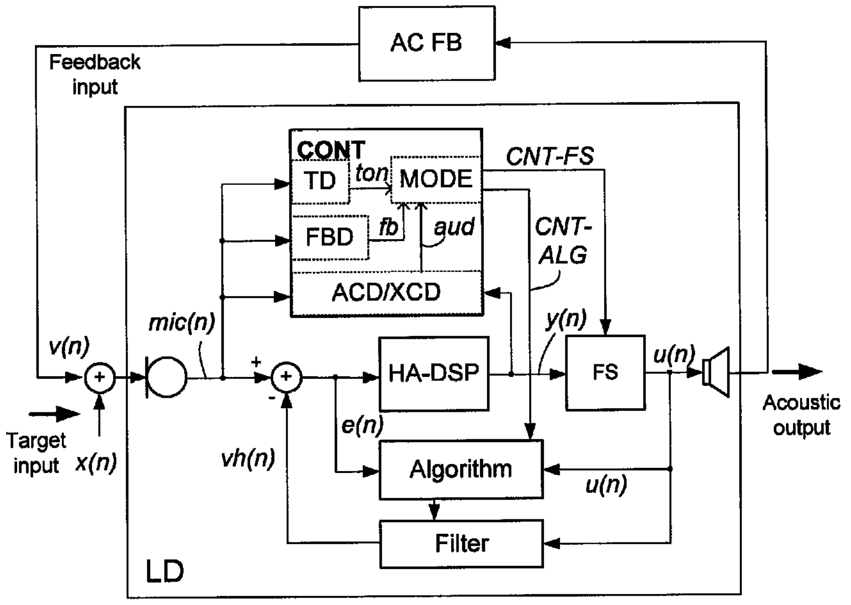
FIG. 8 shows a further embodiment of an audio processing device according to the present disclosure.

FIG. 8 shows a further embodiment of an audio processing device according to the present disclosure. The embodiment of FIG. 8 is similar to the embodiment of FIG. 2D. The embodiments differ in that functional blocks ACD/XCD, TD, FBD, MODE of the control unit CONT are illustrated in FIG. 8, while the mode input of FIG. 2D is absent (implemented via detectors). Further, the control output CNT of FIG. 2D for controlling the frequency compression unit (FS) and the adaptive algorithm (Algorithm) of the feedback estimation system (Algorithm, Filter) is in FIG. 8 split into separate signals CNT-FS and CNT-ALG, respectively.

The application of a frequency shift to a signal of the forward path to de-correlate input and output signals in general becomes more and more audible as the content of tonal components in the input signal increases. The control unit CONT of FIG. 8 comprises an audibility detector based on inputs tapped from the forward path. The auto-correlation or cross-correlation detector (ACD/XCD) will sense tonal components and is hence in the present embodiment used as an audibility detector. The audibility detector (ACD/XCD) provides output signal and indicative of whether or not artefacts introduced by a possible applied frequency shift and/or an update of a feedback path estimate are audible. Such (possibly frequency dependent) threshold values (audible/in-audible) of auto-correlation and/or cross-correlation can be determined by experiment and stored in the listening device in advance of its normal use.

The control unit CONT of FIG. 8 further comprises a tone detector (TD), and a feedback detector (FBD). The tone detector (TD) identifies tonal components in the spectrum of a signal of the forward path, e.g. the electric input sound signal (mic(n) in FIG. 8) and provides output signal ton indicative of whether or not a tonal component (as given by a predefined width and amplitude) is present in the input signal. The feedback detector (FBD) detects whether feedback is present in a signal of the forward path (here signal mic(n) in FIG. 8) at a given point in time as indicated by output signal fb. In an alternative implementation, the tone detector (TD) is operationally connected to the feedback detector (FBD), via signal ton, and the feedback detector (FBD) detects whether a given tonal component in a signal of the forward path is due to feedback or present in the target signal, as indicated by output signal fb.

The control unit CONT of FIG. 8 further comprises a MODE unit for determining a specific mode of operation of the de-correlation unit (FS) and the adaptive algorithm (Algorithm) of the feedback estimation system. The MODE unit bases its mode control on inputs from the detectors of the control unit (CONT), i.e. the tone detector (TD), the feedback detector (FBD) and audibility detector (ACD/XCD) in the form of their respective output signals aud, ton and fb. An implementation of three different modes of operation (termed FAST, STABLE and DYNAMIC, respectively) as also used in the above Example 1 are defined by the table below, where the detector output signals aud, ton and fb are assumed to be binary, to take on only two logic values YES or NO (or 1 and 0). They may alternatively be non-binary.

| Ton | fb | aud | Mode |
|---|---|---|---|
| Yes | Yes | Yes | FAST |
| Yes | No | No | STABLE |
| No | No | No | DYNAMIC |
| No | Yes | Yes | FAST |
| No | Yes | No | FAST |
| Yes | Yes | No | FAST |
| Yes | No | Yes | STABLE |
| No | No | Yes | DYNAMIC, Reduce AR/FS |

DYNAMIC mode: When the environment allows, the estimation of the feedback path is regularly updated and a frequency shift is applied. Frequency shift allows the system to update the feedback path used by the DFC while rendering the system more resistant to external tonal input. Because of the (inherent) risk of producing disturbing artefacts when applying frequency shifts, it is only used when it is estimated that sound quality is not at risk. In the DYNAMIC mode, where no feedback is detected, de-correlation (frequency shift, FS) is applied with a first predetermined amount ($FS_1$) to a signal of the forward path and the adaptive algorithm of the feedback estimation system is updated with a predetermined first adaptation rate ($AR_1$), if no audible artefacts are detected (aud=No). If audible artefacts are detected (aud=Yes), the amount of de-correlation (FS) and/or the adaptation rate AR is/are reduced. Such scheme is e.g. reflected in FIG. 5C, where aud=Yes for AC>ACTh2*x* (XC>XCth2*x*).

STABLE mode: In principle, the feedback path needs to be continuously updated to get a precise estimate, but when the sound environment contains many tonal inputs (ton=yes) or the system gets closer to the feedback margin, the small errors in the estimates will have greater consequences for sound quality. In these cases, where no feedback is detected (fb=No), frequency shift is not active (FS=0) and we cease to update the feedback path estimate (AR=0) and instead maintain the last good estimate and use this for inversion.

In the FAST mode: Feedback is assumed to be present (fb=yes). Frequency shift is applied with a second predetermined amount ($FS_{max}$ than the first frequency shift $FS_1$ of the DYNAMIC mode), which allows a very fast update of the feedback path with a second adaptation rate $AR_2$ (larger than the first adaptation rate $AR_1$ of the DYNAMIC mode) and increases resistance to feedback.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims and equivalents thereof. The de-correlation of a signal of the forward path is in the present application generally exemplified by frequency shift (frequency modulation or frequency compression). It may, however, be based on other principles, e.g. the inclusion of noise like components (e.g. the addition of a noise signal) or by other kinds of modulation, e.g. phase or amplitude modulation.

REFERENCES

EP 1148016 A1

EP 1 718 110 A1

EP 2 237 573 A1

[Joson et al., 1993] Harry Alfonso L. Joson, Futoshi Asano, Yōiti Suzuki, and Toshio Sone, *Adaptive feedback cancellation with frequency compression for hearing aids*, J. Acoust. Soc. Am., Vol. 94 (6), December 1993.

U.S. Pat. No. 5,748,751

U.S. Pat. No. 7,106,871 [Ma et al.; 2011] Guilin Ma, Fredrik Gran, Finn Jacobsen, Finn Thomas Agerkvist, *Adaptive Feedback Cancellation With Band-Limited LPC Vocoder in Digital Hearing Aids*, IEEE Transactions on Audio, Speech and Language Processing, Vol. 19, No. 4, May 2011.

WO 2009/124550 A1

US 2009/028367 A1

WO 2007/113282 A1

The invention claimed is:

1. An audio processing device comprising at least one input transducer for picking up a sound signal and converting it to at least one electric input signal and at least one output transducer for converting an electric output signal to an output sound, a forward path being defined between the at least one input transducer and the at least one output transducer, the forward path comprising a signal processing unit for processing the at least one electric input signal or a signal derived therefrom and providing a processed output signal and a de-correlation unit for de-correlating the electric output signal and the electric input signal; the audio processing device further comprising an analysis path in parallel to all or a part of the forward path, the analysis path comprising a feedback estimation system for estimating feedback from the at least one output transducer to the at least one input transducer and providing a corresponding feedback estimation signal, the feedback estimation system comprising an adaptive filter comprising a variable filter part for filtering an input signal according to variable filter coefficients and an algorithm part, the algorithm part comprising an adaptive algorithm for dynamically updating said filter coefficients, a control unit for controlling said de-correlation unit and said adaptive algorithm, and a correlation detection unit for determining a) the autocorrelation of a signal of the forward path and providing an AC-value and/or b) the cross-correlation between two different signals of the forward path and providing an XC-value, wherein the control unit is configured to base or influence its control of said de-correlation unit and said adaptive algorithm on said AC-value and/or said XC-value.

2. An audio processing device according to claim 1 wherein the control unit is configured to apply de-correlation and adaptation rate according to a predefined scheme including different AC- and/or XC-values.

3. An audio processing device according to claim 1 wherein the control unit is configured to decrease the adaptation rate with increasing AC-value and/or XC-value.

4. An audio processing device according to claim 1 wherein the control unit is configured to decrease the adaptation rate with increasing AC-value and/or XC-value, when the AC-value and/or the XC-value is in the range between a first value and a second value, and to decrease the adaptation rate to zero when the AC-value and/or the XC-value is larger than a predefined threshold value larger than or equal to said second value.

5. An audio processing device according to claim 1 comprising a feedback detector configured to indicate whether a given frequency component of a signal of the forward path has its origin in an external signal or in feedback and to provide a control signal to the control unit, and where the control unit is configured to control said de-correlation unit and said adaptive algorithm in dependence of said control signal.

6. An audio processing device according to claim 5 wherein the control unit is configured to increase the adaptation rate and/or to increase the amount of de-correlation when a control signal from the feedback detector indicates that the frequency component in question is due to feedback.

7. An audio processing device according to claim 1 wherein the de-correlation unit is configured to introduce a modulation of a signal of the forward path, in the form of frequency and/or phase and/or amplitude modulation.

8. An audio processing device according to claim 1 wherein the de-correlation unit is configured to introduce a frequency shift in a signal of the forward path.

9. An audio processing device according to claim 1 wherein the control unit is configured to control adaptation rate of the adaptive algorithm and the amount of de-correlation applied to a signal of the forward path at a given point in time in dependence of current characteristics of the signal.

10. An audio processing device according to claim 9 wherein current characteristics of a signal of the forward path comprises its frequency spectrum.

11. An audio processing device according to claim 9 comprising a frequency analyzing unit for analyzing a frequency spectrum of the electric input signal or a signal derived therefrom.

12. An audio processing device according to claim 11 wherein the frequency analyzing unit is configured to determine a fundamental frequency or to determine one or more dominant frequency bands comprising a predefined fraction of the total power of the power spectrum of said electric input signal at a given point in time.

13. An audio processing device according to claim 11 wherein the maximum size of a frequency shift of the de-correlation unit is controlled depending on the analysis of the frequency spectrum relative to a fundamental frequency or to a dominant frequency band of the current frequency spectrum.

14. An audio processing device according to claim 1 wherein pre-determined maximum values or an algorithm for determining such maximum values of de-correlation at different frequencies are stored in a memory of the audio processing device, such values being related to audibility to ensure in-audibility or minimize audibility of the de-correlation.

15. An audio processing device according to claim 14 wherein the control unit is configured to—for a given value of the correlation measure—determine a maximum adaptation rate to be applied to the adaptive algorithm for estimating feedback based on the maximum amount of de-correlation that can be applied to a signal of the forward path at a given point in time without being audible.

16. An audio processing device according to claim 10 comprising a table or an algorithm for providing corresponding values of adaptation rate and amount of de-correlation to be used by the control unit at the occurrence of corresponding values of a de-correlation measure and dominant frequencies of the current frequency spectrum related to signals of the forward path.

17. An audio processing device according to claim 12 wherein the control unit is configured to control the de-correlation unit and/or the adaptive algorithm depending on a bandwidth of a dominant frequency of the current frequency spectrum.

18. An audio processing device according to claim 1 wherein the control unit is configured to provide that the de-correlation unit is inactive AND to allow the adaptive algorithm to adapt the feedback estimate according to a normal scheme, when the AC-values and/or the XC-values are below a predefined first threshold value.

19. An audio processing device according to claim 1 wherein the control unit is configured to provide that the de-correlation unit is active AND to allow the adaptive algorithm to adapt the feedback estimate according to a normal scheme, when the AC-values and/or the XC-values are in a range above a predefined first threshold value and below a second predefined threshold value.

20. An audio processing device according to claim 1 wherein the control unit is configured to provide that the de-correlation unit is inactive AND the adaptive algorithm is inactive when the AC-values and/or the XC-values are larger than a predefined threshold value.

21. An audio processing device according to claim 1 comprising a memory, and being configured to store a number of previous estimates of the feedback path, in order to be able to rely on a previous estimate, if a current estimate is judged to be less optimal.

22. An audio processing device according to claim 1 configured to operate in several modes, wherein one of the modes of operation is a Stable mode, wherein the update rate of the adaptive algorithm is stopped and a previous set of parameters is used to estimate the feedback path.

23. An audio processing device according to claim 22 wherein in the Stable mode de-correlation is decreased to a minimum value.

24. An audio processing device according to claim 22 wherein the Stable mode is entered, if no feedback is detected to be present in an acoustic environment comprising tonal components representing speech or music.

25. A method of controlling an update algorithm of an adaptive feedback estimation system in an audio processing device, the audio processing device comprising at least one input transducer for picking up a sound signal and converting it to at least one electric input signal and at least one output transducer for converting an electric output signal to an output sound, a forward path being defined between the at least one input transducer and the at least one output transducer, the forward path comprising a signal processing unit for processing the at least one electric input signal or a signal derived therefrom and providing a processed output signal and a de-correlation unit for de-correlating the electric output signal and the electric input signal, the method comprising providing an estimate of the feedback from the at least one output transducer to the at least one input transducer by providing an adaptive algorithm for dynamically updating filter coefficients of a variable filter with a controllable adaption rate;

determining a) the auto-correlation of a signal of the forward path and providing an AC-value and/or b) the cross-correlation between two different signals of the forward path and providing an XC-value;

controlling said de-correlation unit and said adaptive algorithm dependent on said AC-value and/or said XC-value.

26. An audio processing device as claimed in claim 1, comprising a hearing aid.

27. A data processing system comprising a processor and program code means for causing the processor to perform the steps of the method of claim 25.

* * * * *